(12) United States Patent
Arya et al.

(10) Patent No.: US 10,722,293 B2
(45) Date of Patent: Jul. 28, 2020

(54) SURGICAL DEVICE WITH AN END EFFECTOR ASSEMBLY AND SYSTEM FOR MONITORING OF TISSUE BEFORE AND AFTER A SURGICAL PROCEDURE

(71) Applicant: COVIDIEN LP, Mansfield, MA (US)

(72) Inventors: Shobhit Arya, Berkshire (GB); Neil T. Clancy, London (GB); Daniel S. Elson, London (GB); George B. Hanna, Middlesex (GB); Danail V. Stoyanov, London (GB); Xiaofei Du, London (GB)

(73) Assignee: COVIDIEN LP, Mansfield, MA (US)

( * ) Notice: Subject to any disclaimer, the term of this patent is extended or adjusted under 35 U.S.C. 154(b) by 472 days.

(21) Appl. No.: 15/164,701

(22) Filed: May 25, 2016

(65) Prior Publication Data
US 2016/0346034 A1     Dec. 1, 2016

Related U.S. Application Data

(60) Provisional application No. 62/168,356, filed on May 29, 2015.

(51) Int. Cl.
*A61B 18/14* (2006.01)
*A61B 18/22* (2006.01)
(Continued)

(52) U.S. Cl.
CPC .......... *A61B 18/1445* (2013.01); *A61B 18/22* (2013.01); *A61B 2017/00057* (2013.01);
(Continued)

(58) Field of Classification Search
CPC ...... A61B 18/1445; A61B 2017/00057; A61B 2018/00404; A61B 2018/00619;
(Continued)

(56) References Cited

U.S. PATENT DOCUMENTS

D249,549 S    9/1978  Pike
D263,020 S    2/1982  Rau, III
(Continued)

FOREIGN PATENT DOCUMENTS

CN    201299462         9/2009
DE    2415263 A1       10/1975
(Continued)

OTHER PUBLICATIONS

Michael Choti, "Abdominoperineal Resection with the LigaSure Vessel Sealing System and LigaSure Atlas 20 cm Open Instrument"; Innovations That Work, Jun. 2003. (4 pages).
(Continued)

*Primary Examiner* — Jaymi E Della

(57) ABSTRACT

A medical instrument includes a housing and a shaft coupled to the housing. The shaft has a proximal end and a distal end. An end effector assembly is disposed at the distal end of the shaft. The end effector assembly includes first and second jaw members. At least one of the first and second jaw members is movable from a first position wherein the first and second jaw members are disposed in spaced relation relative to one another to at least a second position closer to one another wherein the first and second jaw members cooperate to grasp tissue therebetween. The medical instrument also includes one or more light-emitting elements and one or more light-detecting elements configured to generate one or more signals indicative of tissue reflectance. The one or more light-emitting elements are adapted to deliver light energy to tissue grasped between the first and second jaw members.

10 Claims, 12 Drawing Sheets
(1 of 12 Drawing Sheet(s) Filed in Color)

(51) Int. Cl.
  *A61B 18/00* (2006.01)
  *A61B 17/00* (2006.01)
  *A61B 18/20* (2006.01)
(52) U.S. Cl.
  CPC .............. *A61B 2017/00061* (2013.01); *A61B 2018/0063* (2013.01); *A61B 2018/00404* (2013.01); *A61B 2018/00619* (2013.01); *A61B 2018/00702* (2013.01); *A61B 2018/00785* (2013.01); *A61B 2018/00791* (2013.01); *A61B 2018/00875* (2013.01); *A61B 2018/1455* (2013.01); *A61B 2018/2065* (2013.01); *A61B 2018/20357* (2017.05); *A61B 2018/2211* (2013.01); *A61B 2018/2261* (2013.01)
(58) Field of Classification Search
  CPC .. A61B 2018/0063; A61B 2018/00702; A61B 2018/00875
  See application file for complete search history.

(56) References Cited

U.S. PATENT DOCUMENTS

| | | | |
|---|---|---|---|
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| D384,413 S | 9/1997 | Zlock et al. |
| H1745 H | 8/1998 | Paraschac |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| 7,150,097 B2 | 12/2006 | Sremcich et al. |
| D535,027 S | 1/2007 | James et al. |
| 7,156,846 B2 | 1/2007 | Dycus et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| 7,597,693 B2 | 10/2009 | Garrison |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| 7,771,425 B2 | 8/2010 | Dycus et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| D661,394 S | 6/2012 | Romero et al. |
| D670,808 S | 11/2012 | Moua et al. |
| D680,220 S | 4/2013 | Rachlin |
| 8,777,945 B2 | 7/2014 | Floume et al. |
| 9,084,608 B2 | 7/2015 | Larson et al. |
| 9,211,657 B2 | 12/2015 | Ackley et al. |
| 9,433,461 B2 | 9/2016 | Arya et al. |
| 2003/0171741 A1* | 9/2003 | Ziebol .................. A61B 18/245 606/7 |
| 2010/0218258 A1 | 8/2010 | Hwang et al. |
| 2011/0213349 A1* | 9/2011 | Brown .................... A61B 18/22 606/10 |
| 2011/0251605 A1* | 10/2011 | Hoarau ............... A61B 18/1233 606/34 |
| 2012/0296238 A1 | 11/2012 | Chernov et al. |
| 2012/0296324 A1 | 11/2012 | Chernov et al. |
| 2013/0150842 A1 | 6/2013 | Nau, Jr. et al. |
| 2013/0253489 A1 | 9/2013 | Nau, Jr. et al. |
| 2014/0025053 A1 | 1/2014 | Nau, Jr. et al. |
| 2014/0121507 A1 | 5/2014 | Nau, Jr. |
| 2014/0221995 A1 | 8/2014 | Guerra et al. |
| 2014/0221999 A1 | 8/2014 | Cunningham et al. |
| 2014/0228842 A1 | 8/2014 | Dycus et al. |
| 2014/0230243 A1 | 8/2014 | Roy et al. |
| 2014/0236149 A1 | 8/2014 | Kharin et al. |
| 2014/0243811 A1 | 8/2014 | Reschke et al. |
| 2014/0243824 A1 | 8/2014 | Gilbert |
| 2014/0249528 A1 | 9/2014 | Hixson et al. |
| 2014/0250686 A1 | 9/2014 | Hempstead et al. |
| 2014/0257274 A1 | 9/2014 | McCullough, Jr. et al. |
| 2014/0257283 A1 | 9/2014 | Johnson et al. |
| 2014/0257284 A1 | 9/2014 | Artale |
| 2014/0257285 A1 | 9/2014 | Moua |
| 2014/0276803 A1 | 9/2014 | Hart |
| 2014/0284313 A1 | 9/2014 | Allen, IV et al. |
| 2014/0288549 A1 | 9/2014 | McKenna et al. |
| 2014/0288553 A1 | 9/2014 | Johnson et al. |
| 2014/0330308 A1 | 11/2014 | Hart et al. |
| 2014/0336635 A1 | 11/2014 | Hart et al. |
| 2014/0353188 A1 | 12/2014 | Reschke et al. |
| 2015/0018816 A1 | 1/2015 | Latimer |
| 2015/0025528 A1 | 1/2015 | Arts |
| 2015/0032106 A1 | 1/2015 | Rachlin |
| 2015/0051598 A1 | 2/2015 | Orszulak et al. |
| 2015/0051640 A1 | 2/2015 | Twomey et al. |
| 2015/0066026 A1 | 3/2015 | Hart et al. |
| 2015/0080880 A1 | 3/2015 | Sartor et al. |
| 2015/0080889 A1 | 3/2015 | Cunningham et al. |
| 2015/0082928 A1 | 3/2015 | Kappus et al. |
| 2015/0088122 A1 | 3/2015 | Jensen |
| 2015/0088126 A1 | 3/2015 | Duffin et al. |
| 2015/0088128 A1 | 3/2015 | Couture |
| 2015/0094714 A1 | 4/2015 | Lee et al. |
| 2016/0089198 A1 | 3/2016 | Arya et al. |

FOREIGN PATENT DOCUMENTS

| | | | |
|---|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |

(56) References Cited

FOREIGN PATENT DOCUMENTS

| | | |
|---|---|---|
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A3 | 3/2003 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 09000538 A | 1/1997 |
| JP | 9-122138 A | 5/1997 |
| JP | 0010000195 A | 1/1998 |
| JP | 10-155798 A | 6/1998 |
| JP | 11-47149 | 2/1999 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000-135222 A | 5/2000 |
| JP | 2000342599 A | 12/2000 |
| JP | 2000350732 A | 12/2000 |
| JP | 2001008944 A | 1/2001 |
| JP | 2001-29355 | 2/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-116871 A | 4/2003 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-152663 A | 6/2005 |
| JP | 2005-253789 A | 9/2005 |
| JP | 2005312807 A | 11/2005 |
| JP | 2006-015078 A | 1/2006 |
| JP | 2006-501939 A | 1/2006 |
| JP | 2006-095316 A | 4/2006 |
| JP | 2008-054926 A | 3/2008 |
| JP | 2011125195 A | 6/2011 |
| SU | 401367 A1 | 11/1974 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 02/45589 | 6/2002 |
| WO | 06/021269 A1 | 3/2006 |
| WO | 05110264 A3 | 4/2006 |
| WO | 08/040483 A1 | 4/2008 |
| WO | 20090005850 A1 | 1/2009 |
| WO | 2011/018154 A1 | 2/2011 |
| WO | 2014194317 A1 | 12/2014 |

OTHER PUBLICATIONS

Chung et al., "Clinical Experience of Sutureless Closed Hemorrhoidectomy with LigaSure" Diseases of the Colon & Rectum vol. 46, No. 1 Jan. 2003, pp. 87-92.

Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003. (1 page).

Peterson et al. "Comparison of Healing Process Following Ligation with Sutures and Bipolar Vessel Sealing" Surgical Technology International (2001). (8 pages).

"Electrosurgery: A Historical Overview" Innovations in Electrosurgery; Sales/Product Literature; Dec. 31, 2000. (6 pages).

Johnson et al. "Evaluation of a Bipolar Electrothermal Vessel Sealing Device in Hemorrhoidectomy" Sales/Product Literature; Jan. 2004. (1 page).

E. David Crawford "Evaluation of a New Vessel Sealing Device in Urologic Cancer Surgery" Sales/Product Literature 2000. (1 page).

Johnson et al. "Evaluation of the LigaSure Vessel Sealing System in Hemorrhoidectormy" American College of Surgeons (ACS) Clinicla Congress Poster (2000). (1 page).

Muller et al., "Extended Left Hemicolectomy Using the LigaSure Vessel Sealing System" Innovations That Work, Sep. 1999. (4 pages).

Kennedy et al. "High-burst-strength, feedback-controlled bipolar vessel sealing" Surgical Endoscopy (1998) 12:876-878.

Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.

Carus et al., "Initial Experience With the LigaSure Vessel Sealing System in Abdominal Surgery" Innovations That Work, Jun. 2002. (4 pages).

Heniford et al. "Initial Results with an Electrothermal Bipolar Vessel Sealer" Surgical Endoscopy (2000) 15:799-801. (4 pages).

Herman et al., "Laparoscopic Intestinal Resection With the LigaSure Vessel Sealing System: A Case Report"; Innovations That Work, Feb. 2002. (4 pages).

Koyle et al., "Laparoscopic Palomo Varicocele Ligation in Children and Adolescents" Pediatric Endosurgery & Innovative Techniques, vol. 6, No. 1, 2002, pp. 15-19.

W. Scott Helton, "LigaSure Vessel Sealing System: Revolutionary Hemostasis Product for General Surgery"; Sales/Product Literature 1999. (1 page).

LigaSure Vessel Sealing System, the Seal of Confidence in General, Gynecologic, Urologic, and Laparoscopic Surgery; Sales/Product Literature; Apr. 2002. (8 pages).

Joseph Ortenberg "LigaSure System Used in Laparoscopic 1st and 2nd Stage Orchiopexy" Innovations That Work, Nov. 2002. (4 pages).

Sigel et al. "The Mechanism of Blood Vessel Closure by High Frequency Electrocoagulation" Surgery Gynecology & Obstetrics, Oct. 1965 pp. 823-831.

Sampayan et al, "Multilayer Ultra-High Gradient Insulator Technology" Discharges and Electrical Insulation in Vacuum, 1998. Netherlands Aug. 17-21, 1998; vol. 2, pp. 740-743.

Paul G. Horgan, "A Novel Technique for Parenchymal Division During Hepatectomy" The American Journal of Surgery, vol. 181, No. 3, Apr. 2001 pp. 236-237.

Benaron et al., "Optical Time-Of-Flight and Absorbance Imaging of Biologic Media", Science, American Association for the Advancement of Science, Washington, DC, vol. 259, Mar. 5, 1993, pp. 1463-1466.

(56) References Cited

OTHER PUBLICATIONS

Olsson et al. "Radical Cystectomy in Females" Current Surgical Techniques in Urology, vol. 14, Issue 3, 2001. (8 pages).
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal hysterectomy" Obstetrics & Gynecology, vol. 102, No. 1, Jul. 2003, pp. 147-151.
"Reducing Needlestick Injuries in the Operating Room" Sales/Product Literature 2001. (1 page).
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001. (1 page).
Seyfan et al. "Sutureless Closed Hemorrhoidectomy: A New Technique" Annals of Surgery vol. 234 No. 1, Jul. 2001 pp. 21-24.
Levy et al., "Update on Hysterectomy—New Technologies and Techniques" OBG Management, Feb. 2003. (15 pages).
Dulemba et al. "Use of a Bipolar Electrothermal Vessel Sealer in Laparoscopically Assisted Vaginal Hysterectomy" Sales/Product Literature; Jan. 2004. (1 page).
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000. (1 page).
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000. (4 pages).
Levy et al. "Use of a New Energy-based Vessel Ligation Device During Vaginal Hysterectomy" Int'l Federation of Gynecology and Obstetrics (FIGO) World Congress 1999. (1 page).
Barbara Levy, "Use of a New Vessel Ligation Device During Vaginal Hysterectomy" FIGO 2000, Washington, D.C.. (1 page).
E. David Crawford "Use of a Novel Vessel Sealing Technology in Management of the Dorsal Veinous Complex" Sales/Product Literature 2000. (1 page).
Jarrett et al., "Use of the LigaSure Vessel Sealing System for Peri-Hilar Vessels in Laparoscopic Nephrectomy" Sales/Product Literature 2000. (1 page).
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.. (1 page).
McLellan et al. "Vessel Sealing for Hemostasis During Gynecologic Surgery" Sales/Product Literature 1999. (1 page).
U.S. Appl. No. 08/926,869, filed Sep. 10, 1997; inventor: James G. Chandler, Abandoned.
U.S. Appl. No. 09/177,950, filed Oct. 23, 1998; inventor: Randel A. Frazier, abandoned.
U.S. Appl. No. 09/387,883, filed Sep. 1, 1999; inventor: Dale F. Schmaltz, abandoned.
U.S. Appl. No. 09/591,328, filed Jun. 9, 2000; inventor: Thomas P. Ryan, abandoned.
U.S. Appl. No. 12/336,970, filed Dec. 17, 2008; inventor: Paul R. Sremeich, abandoned.
U.S. Appl. No. 14/065,644, filed Oct. 29, 2013; inventor: Reschke, abandoned.
Heniford et al. "Initial Research and Clinical Results with an Electrothermal Bipolar Vessel Sealer" Oct. 1999. (1 page).
PCT Search Report for PCT/US2016/034330 dated Sep. 6, 2016.
Supplementary European Search Report issued by the European Patent Office dated Feb. 14, 2019 in corresponding European Patent Application No. 16804065.7.

* cited by examiner

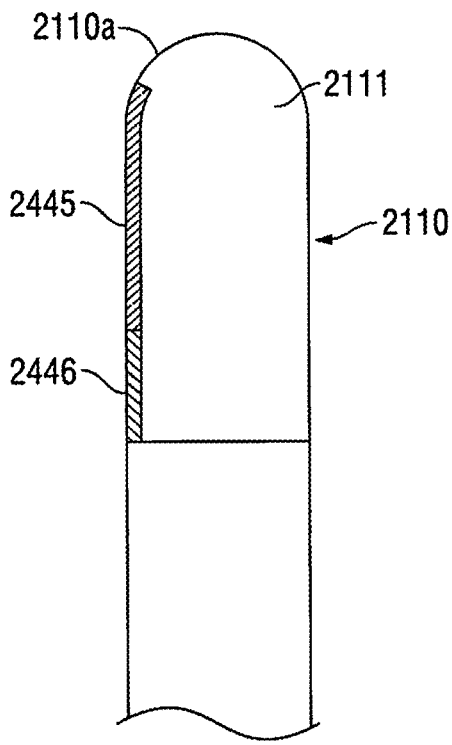
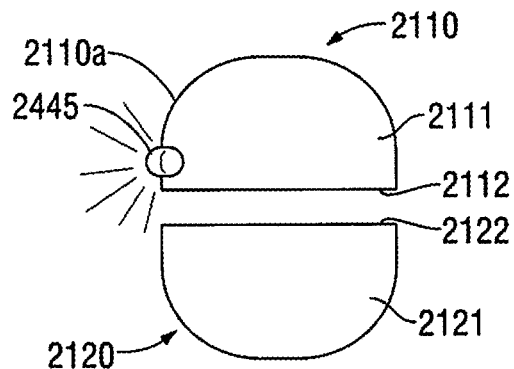
FIG. 9B
FIG. 9A
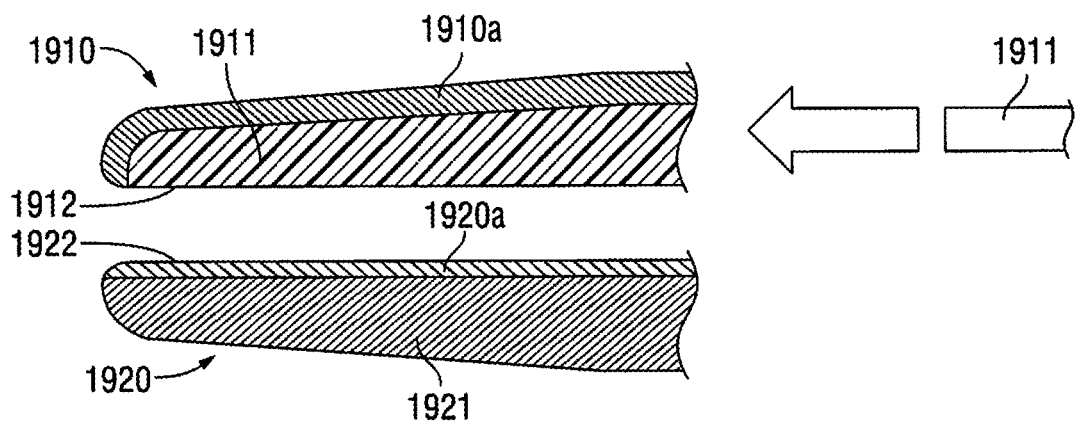
FIG. 10

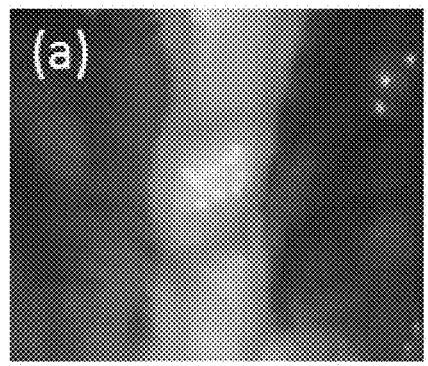
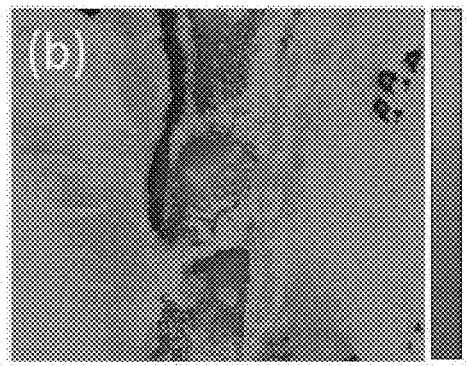
FIG. 14A  FIG. 14B
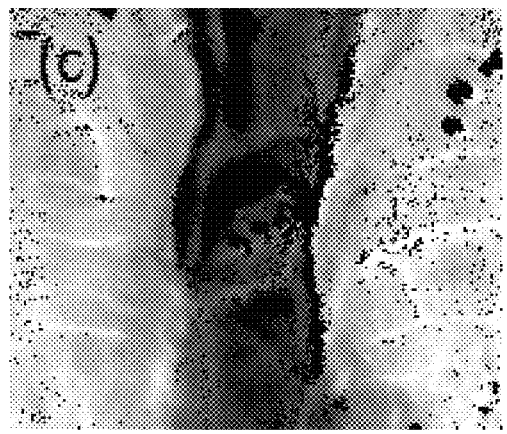
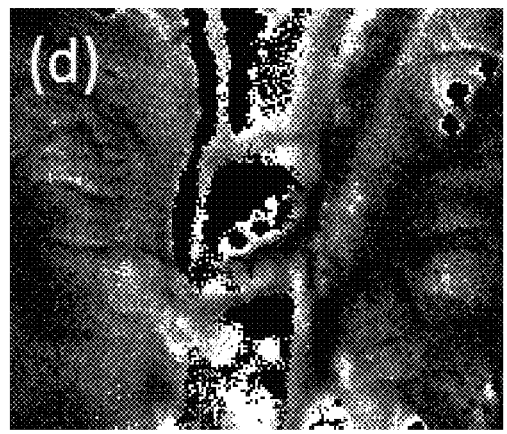
FIG. 14C  FIG. 14D

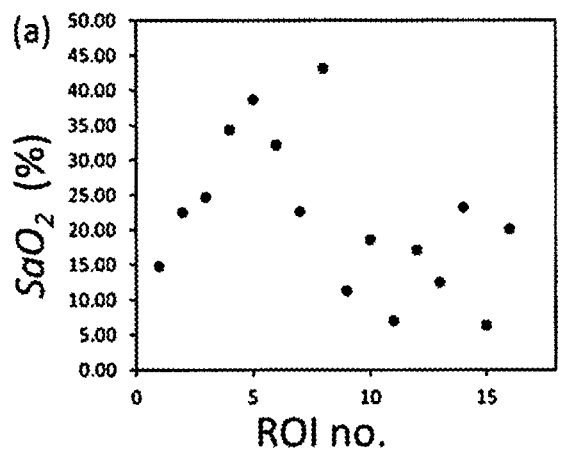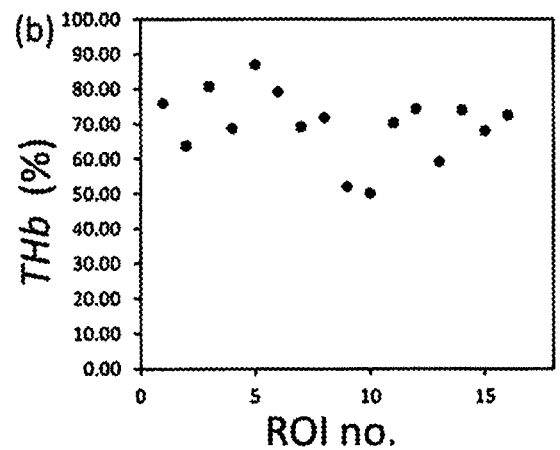
FIG. 16A  FIG. 16B
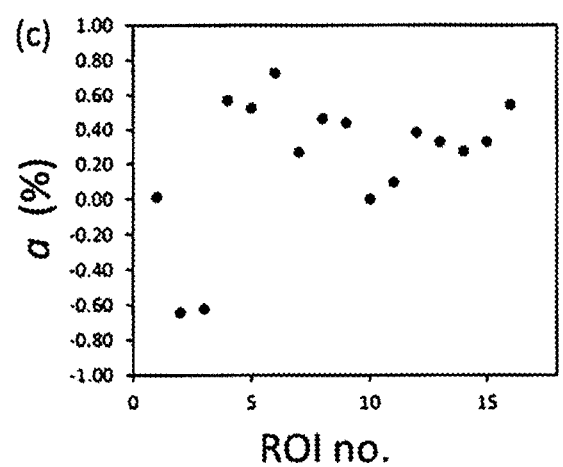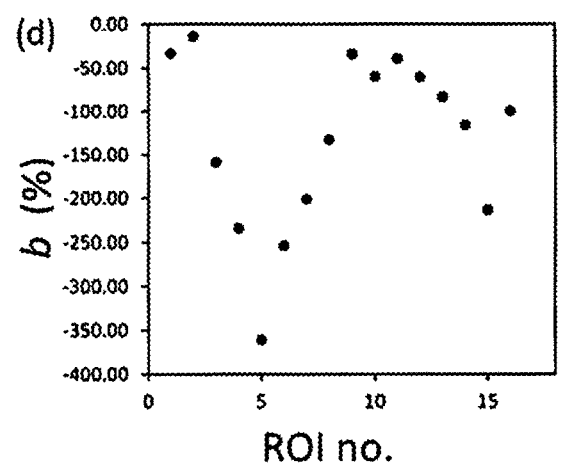
FIG. 16C  FIG. 16D

SURGICAL DEVICE WITH AN END EFFECTOR ASSEMBLY AND SYSTEM FOR MONITORING OF TISSUE BEFORE AND AFTER A SURGICAL PROCEDURE

CROSS-REFERENCE TO RELATED APPLICATION

The present application claims priority to, and the benefit of, U.S. Provisional Application Ser. No. 62/168,356, filed on May 29, 2015, the entire disclosure of which is herein incorporated by reference in its entirety.

BACKGROUND

Technical Field

The present disclosure relates to a surgical forceps having components to treat tissue and/or monitor tissue treatment. More particularly, the present disclosure relates to open or endoscopic surgical forceps adapted to treat tissue and/or to sense tissue properties, and methods and systems for monitoring (e.g., optical, thermal, and/or electrical) of tissue during a surgical procedure.

Description of Related Art

In many surgical procedures, body vessels, e.g., blood vessels, ducts, adhesions, fallopian tubes, or the like are sealed to defunctionalize or close the vessels. Traditionally, staples, clips or sutures have been used to close a body vessel. However, these traditional procedures often leave foreign body material inside a patient. In an effort to reduce foreign body material left within the patient and to more effectively seal the body vessel, energy techniques that seal or fuse tissue by heating the tissue have been employed.

The process of radio-frequency (RF) tissue fusion involves clamping the tissue between two electrodes while holding opposing tissue faces under pressure. A controlled RF voltage is then applied so that the RF current generates heat, and tissue transformations (denaturation and dehydration) are induced by the combined heat and pressure.

Endoscopic or open forceps are particularly useful for sealing since forceps utilize mechanical action to constrict, grasp, dissect and/or clamp tissue. Current vessel-sealing procedures utilize RF treatment to heat and desiccate tissue causing the sealing of vessels or tissue. Other treatment methods are known in the art; however, very few surgical instruments have the capability to treat tissue and monitor tissue treatment without the use of additional surgical instruments.

SUMMARY

Tissue variability is a key challenge in energy-based therapies and surgical procedures with energy-based devices Improved treatment methods may depend on a better understanding of the state of the tissue before and after modifications have occurred, not only allowing the development of effective energy-delivery strategies but also enabling real-time feedback control to control the tissue fusion procedure.

In accordance with an aspect of the present disclosure, a forceps is provided. The forceps includes a housing and a shaft coupled to the housing. The shaft has a proximal end and a distal end. An end effector assembly is disposed at the distal end of the shaft. The end effector assembly includes first and second jaw members. At least one of the first and second jaw members is movable from a first position wherein the first and second jaw members are disposed in spaced relation relative to one another to at least a second position closer to one another wherein the first and second jaw members cooperate to grasp tissue therebetween. The forceps also includes one or more light-emitting elements coupled to either one or both of the first and second jaw members. The one or more light-emitting elements are adapted to deliver light energy to tissue grasped between the first and second jaw members. The forceps also includes one or more light-detecting elements configured to generate one or more signals indicative of tissue reflectance.

In accordance with another aspect of the present disclosure, a forceps is provided and includes a housing, a shaft coupled to the housing, and an end effector assembly disposed at the distal end of the shaft. The end effector assembly includes first and second jaw members. At least one of the first and second jaw members is movable from a first position wherein the first and second jaw members are disposed in spaced relation relative to one another to at least a second position closer to one another wherein the first and second jaw members cooperate to grasp tissue therebetween. The forceps also includes one or more light-emitting elements coupled to either one or both of the first and second jaw members. The one or more light-emitting elements are adapted to deliver light energy to tissue grasped between the first and second jaw members. The forceps also includes a controller configured to control energy delivered to tissue based on the one or more signals indicative of tissue reflectance.

In accordance with another aspect of the present disclosure, a system for treating tissue is provided and includes a forceps. The medical instrument includes a housing and a shaft coupled to the housing. The shaft has a proximal end and a distal end. An end effector assembly is disposed at the distal end of the shaft. The end effector assembly includes first and second jaw members. At least one of the first and second jaw members is movable from a first position wherein the first and second jaw members are disposed in spaced relation relative to one another to at least a second position closer to one another wherein the first and second jaw members cooperate to grasp tissue therebetween. A first tissue-contacting surface is associated with the first jaw member. A second tissue-contacting surface is associated with the second jaw member. One or more light-emitting elements are coupled to one or both of the first and second jaw members. The one or more light-emitting elements are adapted to deliver light energy to tissue grasped between the first and second jaw members. The forceps includes one or more light-detecting elements configured to sense one or more properties of the light energy passing through the tissue, and a controller coupled to the one or more light-detecting elements and the one or more light-emitting elements. The controller is configured to control the forceps based on the at least one property of the light energy sensed by the at least one light-detecting element.

In accordance with another aspect of the present disclosure, a method of treating tissue is provided and includes positioning an end effector assembly including first and second jaw members at a first position within tissue. Each of the first and second jaw members includes a tissue-contacting surface. At least one of the first and second jaw members is movable from a spaced relation relative to the other jaw member to at least one subsequent position wherein the tissue-contacting surfaces cooperate to grasp tissue therebetween. The method also includes activating a light-emitting element associated with one or both of the first and second jaw members to emit light into tissue and evaluating one or more characteristics of the tissue based on a response to light entering the tissue.

As used herein, the term "treat" refers to performing a surgical treatment to tissue including, but not limited to heating, sealing, cutting, sensing and/or monitoring. As used herein, the term "light energy source" refers broadly to include all types of devices that produce light for medical use (e.g., tissue treatment). These devices include lasers, light-emitting diodes (LEDs), lamps, and other devices that produce light anywhere along an appropriate part of the electromagnetic spectrum (e.g., from infrared to ultraviolet). It is also to be understood that the light sources disposed herein may be used interchangeably, such that, if an LED light source is disclosed, a laser light source may also be used, unless stated otherwise.

Various embodiments of the present disclosure provide systems and methods for treating tissue (and/or monitoring of tissue) by delivering light thereto. This may be accomplished by placing a light source in intimate contact with the target tissue. In some embodiments, it may be accomplished by connecting a light source to the target tissue with an optical system designed to transmit the light from the light source to the tissue. Either system may include elements that shape the distribution of optical energy as it impinges on and interacts with the target tissue. As herein, the term "light-emitting elements" denotes any device from which light exits prior to interacting with the target tissue including but not limited to: light sources; the end of a light transmission system terminating at the target tissue; and/or refracting, diffracting, transmitting or reflecting optical elements such as lenses, diffraction gratings, windows and mirrors, and combinations thereof.

In general, the term "laser light source" is interchangeable, in this disclosure, with the terms "laser source," "excitation light source" and "excitation source." Laser light sources may produce light having a wavelength from about 200 nanometers (nm) to about 15,000 nm and include but are not limited to ruby lasers, tunable titanium-sapphire lasers, copper vapor lasers, carbon dioxide lasers, alexandrite lasers, argon lasers such as argon fluoride (ArF) excimer lasers, argon-dye lasers, potassium titanyl phosphate (KTP) lasers, krypton lasers such as krypton fluoride (KrF) excimer lasers, neodymium:yttrium-aluminum-garnet (Nd:YAG) lasers, holmium:yttrium-aluminum-garnet (Ho:YAG) lasers, erbium:yttrium-aluminum-garnet (Er:YAG) lasers, diode lasers, fiber lasers, xenon chloride (XeCl) excimer lasers, tunable thalium lasers, and combinations thereof. Additional light source types also include fiber optic light sources and deuterium light sources.

In some aspects of the present disclosure, light may be generated at multiple wavelengths. For example, Nd:YAG and KTP lasers may be part of a single light source. Nd:YAG with a greater optical depth in tissue may be used for sealing, and KTP with a shorter optical depth may be used for sealing smaller vessels, thinner tissue, or for cutting. As used herein, the term "receiving module" refers to a component or apparatus having the capability of receiving and/or sensing a signal (e.g., light energy and heat energy) and generating an output signal (e.g., indication to a user, control information, parameter setting instruction, etc.). This may occur by analyzing the received signal to generate one or more control signals. In some embodiments, based on the one or more control signals, a controller may adjust operating parameters of an energy source (e.g., laser source, RF generator, etc.) and/or perform other control functions, alarming functions, or other functions in association therewith. The receiving module may also transmit the received signal to some other suitable component (e.g., processor, signal analyzing unit, and/or generator) for signal processing, analysis, etc.

As described in more detail below with reference to the accompanying figures, the present disclosure generally relates to surgical energy-based devices that include an end effector assembly configured to fuse (e.g., seal) and/or separate (e.g., cut) tissue. The present disclosure also provides one or more devices configured to sense and/or monitor tissue and/or energy properties (e.g., tissue impedance, tissue temperature, and tissue fluorescence) before and after treatment to determine whether a treatment will be successful and, when the treatment is complete, efficacy of a tissue seal. Optical sensing provides a better indication of seal quality than existing methods such as electrical impedance measurements. In some embodiments, tissue separation may be accomplished with the same light energy device used for tissue sealing, which eliminates the need for a separate mechanical blade that is traditionally used for tissue separation in jaw members. The present disclosure also provides methods for providing feedback to the user, generator, controller and/or control algorithm with regard to temperature of tissue, electrical impedance of tissue, temporal profile of tissue fluorescence features, jaw closure pressure, jaw positioning, and/or other various feedback information, e.g., multispectral spectrometry. In some embodiments, reflectance data may be used for optimization of the RF energy delivery protocol to avoid excessive tissue thermal damage and/or incomplete tissue fusions.

Any of the following aspects and components thereof of the present disclosure may be interchangeably combined with one or more other embodiments. For example, various disclosed methods and systems for monitoring of tissue and control processes may be utilized with various jaw member embodiments.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Objects and features of the presently-disclosed surgical device with an end effector assembly and the method and system for monitoring of tissue before and after a surgical procedure will become apparent to those of ordinary skill in the art when descriptions of various embodiments thereof are read with reference to the accompanying drawings, of which:

FIG. 9A is a top view of a jaw member including a light dissection element disposed on an outer periphery thereof in accordance with an embodiment of the present disclosure;

FIG. 9B is a front, cross-sectional view of the jaw member of FIG. 9A including a light dissection element disposed on an outer periphery thereof in accordance with an embodiment of the present disclosure;

FIG. 10 is a side, cross-sectional view of an end effector assembly in accordance with another embodiment of the present disclosure;

FIGS. 14A through 14D are example images taken using the multispectral spectroscopy imaging technique in accordance with an embodiment of the present disclosure;

FIGS. 16A through 16D depict percentage differences in parameter values between normal and fused bowel tissue in accordance with an embodiment of the present disclosure.

DETAILED DESCRIPTION

Figure 1A:
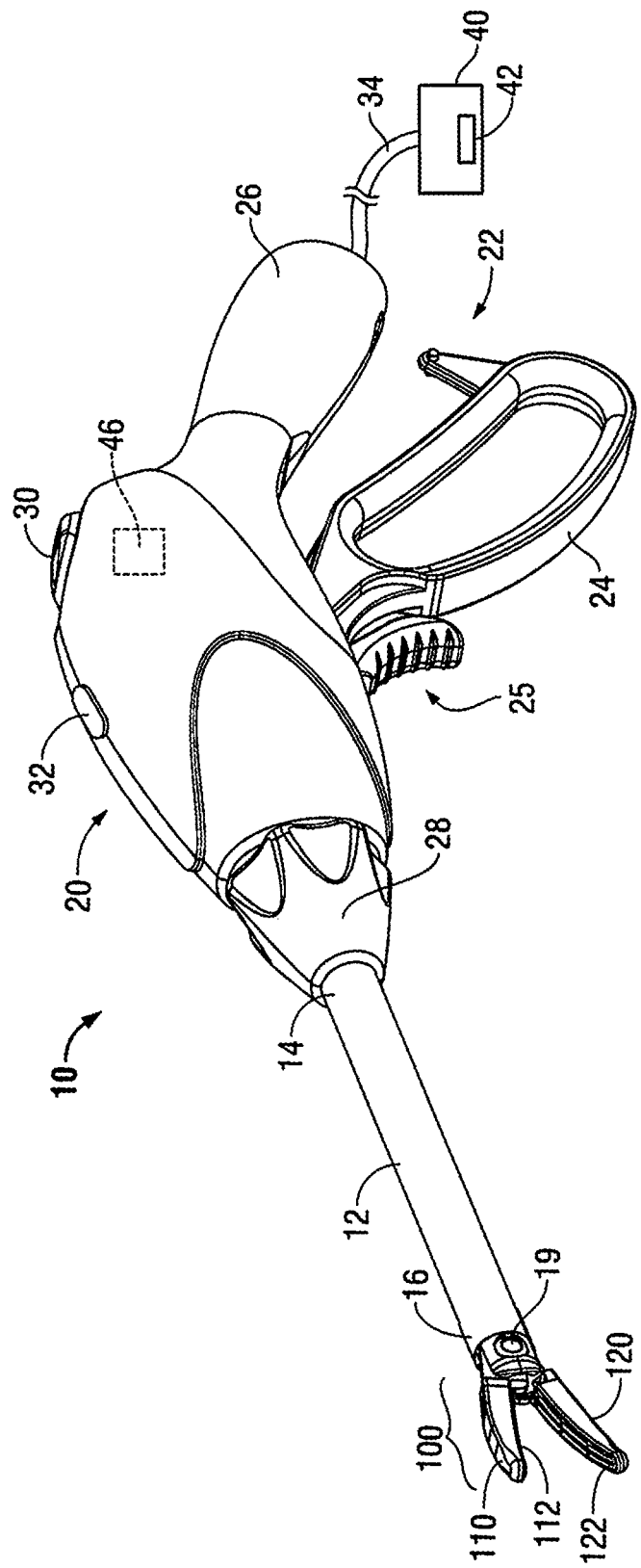
FIG. 1A is a perspective view of an endoscopic forceps having an end effector assembly coupled to the distal end of the forceps in accordance with an embodiment of the present disclosure.

Hereinafter, embodiments of surgical devices with an end effector assembly and methods and systems for monitoring of tissue before and after a surgical procedure of the present disclosure are described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the apparatus, or component thereof, closer to the user and the term "distal" refers to that portion of the apparatus, or component thereof, farther from the user.

This description may use the phrases "in an embodiment," "in embodiments," "in some embodiments," or "in other embodiments," which may each refer to one or more of the same or different embodiments in accordance with the present disclosure.

As it is used in this description, "transmission line" generally refers to any transmission medium that can be used for the propagation of signals from one point to another. A transmission line may be, for example, a wire, a two-wire line, a coaxial wire, a waveguide, a fiber optic line and/or fiber optic bundles.

As it is used herein, "computer" generally refers to anything that transforms information in a purposeful way. Examples of a computer may include: a computer; a personal computer (PC); a portable computer; a laptop computer; a computer having a single processor, multiple processors, or multi-core processors, which may operate in parallel and/or not in parallel; a general purpose computer; a supercomputer; a mainframe; a super mini-computer; a mini-computer; a workstation; a micro-computer; a server; a web appliance; a hybrid combination of a computer and an interactive television; a tablet personal computer; a personal digital assistant (PDA); application-specific hardware to emulate a computer and/or software, such as, for example, a digital signal processor (DSP), a field-programmable gate array (FPGA), an application specific integrated circuit (ASIC), an application specific instruction-set processor (ASIP), a chip, chips, or a chip set; a system on a chip (SoC), or a multiprocessor system-on-chip (MPSoC); an optical computer; a quantum computer; a biological computer; and an apparatus that may accept data, may process data in accordance with one or more stored software programs, and may generate results. For the purposes of this description, the terms "software" and "code" should be interpreted as being applicable to software, firmware, or a combination of software and firmware.

Various embodiments of the present disclosure provide surgical instruments suitable for sealing, cauterizing, coagulating, desiccating, and/or cutting tissue, e.g., vessels and vascular tissue, during a surgical procedure. Embodiments of the presently-disclosed surgical instruments may be configured to provide light energy, which may be suitable for sealing, cauterizing, coagulating, desiccating, and/or cutting tissue. The light energy may be provided in different forms, including but not limited to lasers, light-emitting diode, and any other suitable type of light energy. Embodiments of the presently-disclosed surgical instruments may be configured to provide monopolar electrosurgical energy and/or bipolar electrosurgical energy, which may be suitable for sealing, cauterizing, coagulating, desiccating, and/or cutting tissue, e.g., vessels and vascular tissue. Embodiments of the presently-disclosed surgical instruments may be suitable for utilization in endoscopic surgical procedures and/or suitable for utilization in open surgical applications.

Embodiments of the presently-disclosed surgical instruments may be implemented using a variety of types of energy, e.g., surgical energy at radio frequencies (RF) and/or at other frequencies, optical, and/or thermal energy. Embodiments of the presently-disclosed surgical instruments may be configured to be connectable to one or more energy sources, e.g., laser sources, RF generators, and/or self-contained power sources. Embodiments of the presently-disclosed surgical instruments may be connected through a suitable bipolar cable and/or other transmission line to an electrosurgical generator and/or other suitable energy source, e.g., laser light source.

The multispectral spectroscopy method described herein provides direct insights into tissue constituent and structure on the molecular level by decomposing the reflectance spectrum into contributions from absorbers, such as hemoglobin, and scatterers. The fraction of oxygenated hemoglobin present may be calculated to provide a measure of tissue viability, while relative changes in blood volume and tissue structure may also be determined.

Various embodiments described herein utilize these insights to provide a better understanding of the intrinsic mechanisms for tissue fusion and to provide optical feedback-control methods for heat-induced tissue fusion and improved control methods for tissue fusion procedures in accordance with the present disclosure.

Figure 1B:
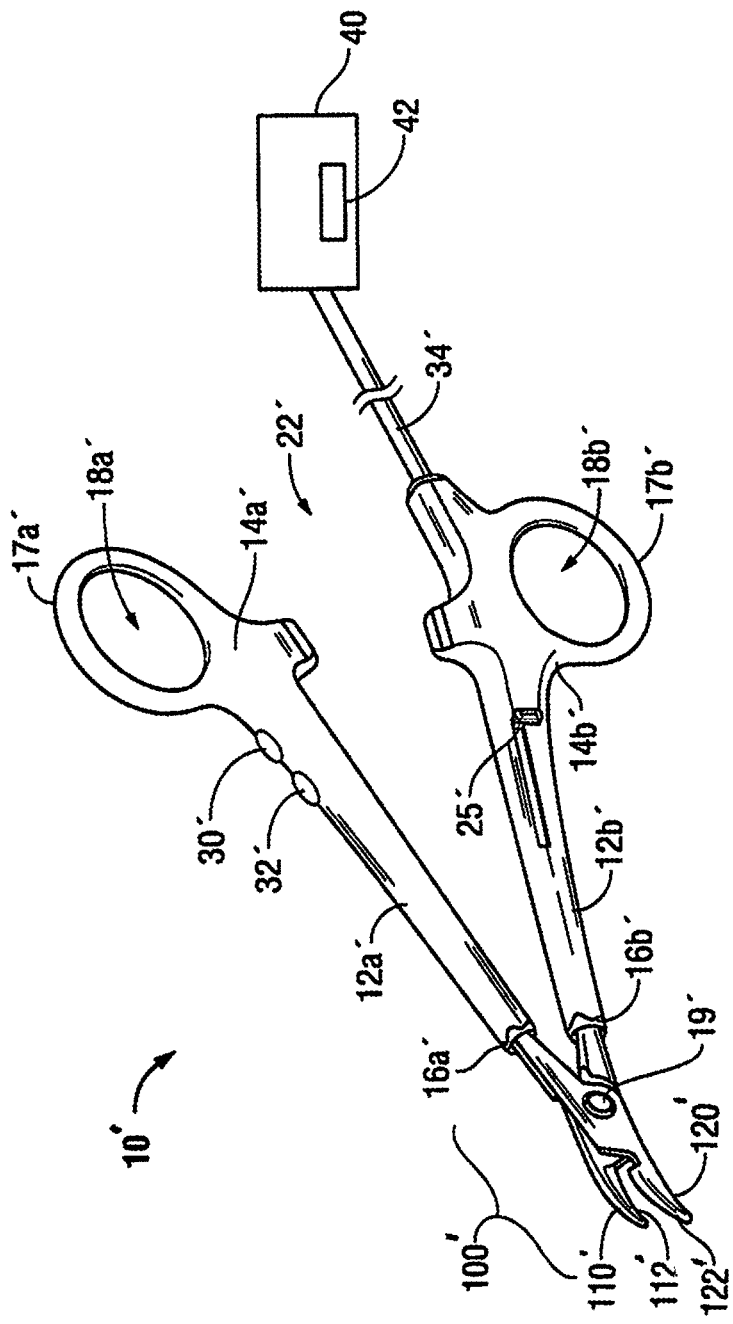
FIG. 1B is a perspective view of an open forceps having a handle assembly and an end effector assembly coupled to the distal end of the handle assembly in accordance with an embodiment of the present disclosure.

FIG. 1A depicts an embodiment of a forceps for use in connection with endoscopic surgical procedures, and an embodiment of an open version of a forceps is shown in FIG. 1B.

For the purposes herein, either an endoscopic instrument or an open surgery instrument may be utilized with any of the embodiments of end effector assemblies described herein. It should be noted that different electrical, optical and mechanical connections and other considerations may apply to each particular type of instrument. However, aspects with respect to the end effector assembly and the operating characteristics thereof remain generally consistent with respect to both the endoscopic or open surgery designs.

Various embodiments of the present disclosure provide an apparatus, system and method for sealing tissue using light energy. Light (e.g., with a wavelength range of from about 200 nm to about 11,000 nm) is used to heat tissue due to the absorption of light into the tissue. Absorption, transmittance, and scattering of light energy depends on the tissue, the state of the tissue (e.g., hydration, disease state, treatment stage, etc.), and the wavelength of the light. In accordance with some embodiments of the present disclosure, these factors are utilized to control the distribution of the energy within the tissue based on an appropriate choice of the wavelength. More specifically, wavelengths that are strongly absorbed by the tissue deposit energy closer to the surface of the tissue, and wavelengths that are weakly absorbed by the tissue are used to deposit a larger fraction of the incident energy deeper in the tissue. In particular, since tissue is relatively transparent to light at certain infrared wavelengths, light energy at infrared frequencies may be used for deeper energy deposition.

In FIGS. 1A and 1B, surgical instruments (generally referred to herein as forceps 10 and open forceps 10') are shown for use with various surgical procedures. Forceps 10 and open forceps 10' may include additional, fewer, or different components than shown in FIGS. 1A and 1B, depending upon a particular purpose or to achieve a desired result.

Forceps 10 includes a transmission line 34, which may connect directly to a light energy source (e.g., energy source 40) for generating light energy adapted to treat tissue. Transmission line 34 (also referred to herein as "cable 34") may be formed from a suitable flexible, semi-rigid, or rigid cable. Cable 34 may be internally divided into one or more cable leads (not shown) each of which transmits energy through their respective feed paths to the end effector assembly 100. Cable 34 may additionally, or alternatively, include an optical fiber configured to transmit light energy and/or control signals to the end effector assembly 100.

Energy source 40 may be any generator suitable for use with surgical devices, and may be configured to output various types of energy, e.g., light energy having a wavelength from about 200 nm to about 11,000 nm Energy source 40 may additionally, or alternatively, be configured to provide RF energy and/or various frequencies of electromagnetic energy.

Energy source 40 may include any laser light source suitable for use with surgical devices. In some embodiments, more than one laser source may be included in the energy source 40, and more than one laser may be used during a surgical procedure. Examples of laser light sources include Thorlabs' diode lasers modules (Thorlabs Inc., Newton, N.J.). Energy source 40 shown in FIG. 1 includes a controller 42, e.g., logic circuit, computer, processor, field programmable gate array, and the like. Controller 42 may include a microprocessor having a memory (not explicitly shown), which may be volatile type memory (e.g., RAM) and/or non-volatile type memory (e.g., flash media, disk media, etc.).

In some embodiments, the controller 42 is configured to provide timing, wavelength, and/or power control of the one or more lasers. Energy source 40 may include one or more mechanisms for laser selection, filtering, temperature compensation, and/or Q-switching operations. In some embodiments, the energy source 40 may include a function generator and optical shutter used to modulate a continuous-wave laser to generate pulsed output. Various embodiments of the forceps 10 utilizing the aforementioned light energy are discussed in more detail below.

In some embodiments, wherein the energy source 40 is configured to provide RF energy, the controller 42 may additionally, or alternatively, utilize one or more signals indicative of conditions and/or operational parameters (e.g., tissue impedance, temperature, jaw member opening angle, force applied to tissue, thickness of tissue, and/or and tissue fluorescence) to adjust one or more operating parameters associated with the energy source 40 (e.g., duration of application of RF energy, mode of operation, power, current, and voltage) and/or instruct the energy source 40 to perform other control functions, alarming functions, or other functions in association therewith. Examples of generators that may be suitable for use as a source of RF energy are commercially available under the trademarks FORCE EZ™, FORCE FX™, and FORCE TRIAD™ offered by Covidien Surgical Solutions of Boulder, Colo.

Forceps 10 is configured to support an end effector assembly (e.g., end effector assembly 100). Forceps 10 includes a housing 20, a handle assembly 22, a trigger assembly 25, a rotatable assembly 28, and end effector assembly 100. End effector assembly 100 may include any feature or combination of features of the jaw member embodiments disclosed herein. One or more components of the forceps 10, e.g., housing 20, rotatable assembly 28, and/or end effector assembly 100, may be adapted to mutually cooperate to grasp, seal, divide and/or sense tissue, e.g., tubular vessels and vascular tissue. In some embodiments, trigger assembly 25 may be configured to actuate a cutting function of the forceps 10 or to actuate another component, as described in more detail below.

End effector assembly 100, which is described in more detail later in this disclosure, generally includes two jaw members 110 and 120 disposed in opposing relation relative to one another. One or both of the jaw members 110 and 120 are movable from a first position wherein the jaw members 110 and 120 are disposed in spaced relation relative to one another to a second position wherein the jaw members 110 and 120 cooperate to grasp tissue therebetween.

Forceps 10 includes an elongated shaft 12 having a distal portion 16 configured to mechanically engage end effector assembly 100. The proximal end 14 of shaft 12 is received within housing 20, and connections relating thereto are shown and described in commonly-assigned U.S. Pat. No. 7,150,097 entitled "Method Of Manufacturing Jaw Assembly For Vessel Sealer And Divider," commonly-assigned U.S. Pat. No. 7,156,846 entitled "Vessel Sealer And Divider For Use With Small Trocars And Cannulas," commonly-assigned U.S. Pat. No. 7,597,693 entitled "Vessel Sealer And Divider For Use With Small Trocars And Cannulas," and commonly-assigned U.S. Pat. No. 7,771,425 entitled "Vessel Sealer And Divider Having A Variable Jaw Clamping Mechanism," the disclosures of which are herein incorporated by reference in their entireties. Rotatable assembly 28 is mechanically associated with shaft 12 such that rotational movement of rotatable assembly 28 imparts similar rotational movement to shaft 12 that, in turn, rotates end effector assembly 100.

Handle assembly 22 includes a fixed handle 26 and a movable handle 24. In some embodiments, the fixed handle 26 is integrally associated with the housing 20, and the movable handle 24 is selectively movable relative to the fixed handle 26. Movable handle 24 of the handle assembly 22 is ultimately connected to the drive assembly (not shown). As can be appreciated, applying force to move the movable handle 24 toward the fixed handle 26 pulls a drive sleeve (not shown) proximally to impart movement to the jaw members 110 and 120 from an open position, wherein the jaw members 110 and 120 are disposed in spaced relation relative to one another, to a clamping or closed position, wherein the jaw members 110 and 120 cooperate to grasp tissue therebetween. Examples of handle assembly embodiments of the forceps 10 are described in the above-mentioned, commonly-assigned U.S. Pat. Nos. 7,150,097, 7,156,846, 7,597,693 and 7,771,425.

In some embodiments, the end effector assembly 100 is configured as a unilateral assembly that includes a stationary jaw member (e.g., jaw member 120) mounted in fixed relation to the shaft 12 and a pivoting jaw member (e.g., jaw member 110) movably mounted about a pin 19. Jaw members 110 and 120 may be curved at various angles to facilitate manipulation of tissue and/or to provide enhanced line-of-sight for accessing targeted tissues. Alternatively, the forceps 10 may include a bilateral assembly, i.e., both jaw members 110 and 120 move relative to one another.

Figure 2A:
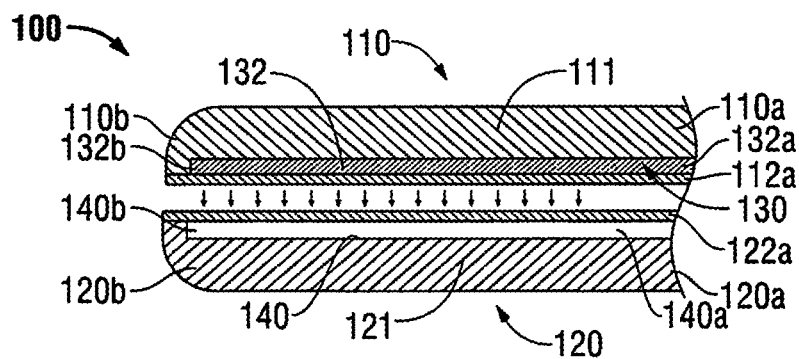
FIG. 2A is a side, cross-sectional view of an end effector assembly in accordance with an embodiment of the present disclosure.
Figure 2B:
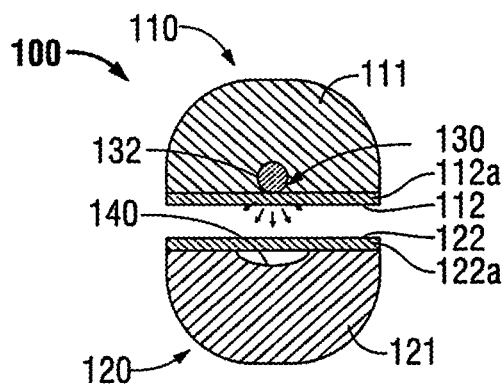
FIG. 2B is a front, cross-sectional view of the end effector assembly of FIG. 2A.

Jaw members 110 and 120, as shown for example in FIG. 2B, include a tissue-contacting surface 112 and 122, respectively, arranged in opposed relation relative to one another. Tissue-contacting surfaces 112 and 122 cooperate to grasp and seal tissue held therebetween upon application of energy from energy source 40. In some embodiments, tissue-contacting surfaces 112 and 122 are connected to the energy source 40 such that light energy can be transmitted to and/or through the tissue held therebetween.

First and second switch assemblies 30 and 32 are configured to selectively provide light energy to end effector assembly 100. More particularly, the first switch assembly 30 may be configured to perform a first type of surgical procedure (e.g., seal, cut, and/or sense) and a second switch assembly 32 may be configured to perform a second type of surgical procedure (e.g., seal, cut, and/or sense). It should be noted that the presently-disclosed embodiments may include any number of suitable switch assemblies and are not limited to only switch assemblies 30 and 32. It should further be noted that the presently-disclosed embodiments may be configured to perform any suitable surgical procedure and are not limited to only sealing, cutting and sensing.

Forceps 10 generally includes a controller 46. In some embodiments, as shown in FIG. 1, the controller 46 is formed integrally with the forceps 10. In other embodiments, the controller 46 may be provided as a separate component coupled to the forceps 10. Controller 46 may include any type of computing device, computational circuit, or any type of processor or processing circuit capable of executing a series of instructions that are stored in a memory. Controller 46 may be configured to control one or more operating parameters associated with the energy source 40 based on one or more signals indicative of user input, such as generated by the first and second switch assemblies 30 and 32 and/or one or more separate, user-actuatable buttons or switches. Examples of switch configurations that may be suitable for use with the forceps 10 include, but are not limited to, pushbutton, toggle, rocker, tactile, snap, rotary, slide and thumbwheel. In some embodiments, the forceps 10 may be selectively used in either a monopolar mode or a bipolar mode by engagement of the appropriate switch.

First and second switch assemblies 30 and 32 may also cooperate with the controller 42, which may be configured to automatically trigger one of the switches to change between a first mode (e.g., sealing mode) and a second mode (e.g., cutting mode) upon the detection of one or more parameters or thresholds. In some embodiments, the controller 42 (and/or the controller 46) is configured to receive feedback information, including various sensor feedback with regard to temperature of tissue, electrical impedance of tissue, jaw closure pressure, jaw positioning, and/or other various feedback information, e.g., using multispectral spectroscopy, and to control the energy source 40 based on the feedback information.

Embodiments of the present disclosure allow the jaw members 110 and 120 to seal and/or cut tissue using light energy. In some embodiments, the controller 42 may include a feedback loop that indicates when a tissue seal is complete based upon one or more of the following parameters: tissue temperature, optical sensing, change in impedance of the tissue over time and/or changes in the optical or electrical power or current applied to the tissue over time, rate of change of these properties and combinations thereof. An audible or visual feedback monitor may be employed to convey information to the surgeon regarding the overall seal quality and/or the completion of an effective tissue seal.

Referring now to FIG. 1B, an open forceps 10' is depicted and includes end effector assembly 100' (similar to forceps 10) that is attached to a handle assembly 22' that includes a pair of elongated shaft portions 12a' and 12b'. Each elongated shaft portion, 12a' and 12b', respectively, has a proximal end 14a' and 14b', respectively, and a distal end 16a' and 16b', respectively. The end effector assembly 100' includes jaw members 110' and 120' coupled to distal ends 16a' and 16b' of shafts 12a' and 12b', respectively. The jaw members 110' and 120' are connected about pivot pin 19' that allows jaw members 110' and 120' to pivot relative to one another from the first to second positions for treating tissue (as described above). Tissue-contacting surfaces 112' and 122' are connected to opposing jaw members 110' and 120'.

Each shaft 12a' and 12b' includes a handle 17a' and 17b', respectively, disposed at the proximal end 14a' and 14b' thereof. Handles 17a' and 17b' facilitate movement of the shafts 12a' and 12b' relative to one another which, in turn, pivot the jaw members 110' and 120' from the open position wherein the jaw members 110' and 120' are disposed in spaced relation relative to one another to the clamping or closed position wherein the jaw members 110' and 120' cooperate to grasp tissue therebetween.

In some embodiments, one or both of the shafts, e.g., shaft 12a', includes a first switch assembly 30' and a second switch assembly 32'. First and second switch assemblies 30' and 32' may be configured to selectively provide energy to the end effector assembly 100'. More particularly, the first switch assembly 30' may be configured to perform a first type of surgical procedure (e.g., seal, cut, or sense) and second switch assembly 32' may be configured to perform a second type of surgical procedure (e.g., seal, cut, or sense). In some embodiments, both or one of the shafts, e.g., shaft 12b', may include a trigger assembly 25' for actuation of an additional laser fiber (e.g., laser fiber 230a and/or 230b shown in FIG. 3).

With continued reference to FIG. 1B, forceps 10' is depicted having a cable 34' that connects the forceps 10' to energy source 40. In some embodiments, cable 34' is internally divided within the shaft 12b' to transmit light energy through various transmission paths to one or more components of end effector assembly 100'.

FIGS. 2A and 2B illustrate an end effector assembly 100' according to an embodiment of the present disclosure, which is configured for use with either instrument 10 or instrument 10', discussed above or any other suitable surgical instrument. However, for purposes of simplicity and consistency, end effector assembly 100' is described hereinbelow with reference to instrument 10.

In some embodiments, as shown for example in FIGS. 2A and 2B, jaw members 110 and 120 include proximal ends 110a and 120a, respectively, distal ends 110b and 120b, respectively, and a groove or channel 130 and 140, respectively, defined therebetween. Jaw member 110 includes a light-diffusing element 132 that is disposed on or along tissue-contacting surface 112. The light-diffusing element 132 may be made from any suitable light diffusing material, such as frosted sapphire crystal. The light-diffusing element 132 is disposed within channel 130. Tissue-contacting surfaces 112 and 122 may include a reflective surface disposed thereon. In some embodiments, the surface includes, but is not limited to polished metal, coating or any other material that is adapted to reflect light.

In other embodiments, tissue-contacting surfaces 112 and 122 may also include a coating or cover 112a and 122a. In some embodiments, the coatings 112a and 122a may be formed from a light absorbing material (e.g., a light absorbent coating), a transparent material, a scattering material, or a reflective material. In some embodiments, the coating 112a may be formed from one material (e.g., a transparent material) while the coating 122a may be formed from a different material (e.g., a light absorbent or reflective material). In some embodiments, the coatings 112a and 122a may both be formed from the same material, such as a reflective material. Providing both tissue-contacting surfaces 112 and 122 with reflective surfaces increases absorption of the light being supplied to the tissue since the light passes multiple times therethrough, which may shorten the treatment time.

In some embodiments, the coatings 112a and 122a may include a gel or another biocompatible film disposed thereon. The gel or the film may include a dye of a specific color designed to absorb light energy at a specific wavelength. In some embodiments, the gel may be applied to the tissue prior to treatment.

In other embodiments, the coatings 112a and 122a are absorbent coatings formed from a thermochromic material configured to increase absorption properties as temperature increases. As used herein, the term "thermochromic" generally refers to any material that changes color in response to a change in temperature. As the temperature of the jaw members 110 and 120 increases during application of energy, the absorbent coatings 112a and 122a become progressively more absorbing and provide more heat to the tissue.

The light-diffusing element 132 may be coupled to energy source 40 via cable 34, which may include one or more a light transporting or light generating fibers therewithin. In some embodiments, the energy source 40 is adapted to generate a light of a desired wavelength from about 200 nm to about 11,000 nm and transmit the light energy along cable 34 to the forceps 10, 10' and, more specifically, to the light-diffusing element 132.

Light-diffusing element 132 may have a substantially cylindrical or conical shape and may be formed from a suitable light conducting material (e.g., sapphire crystal, crystal glass, plastic fiber, and the like). More specifically, the light-diffusing element 132 may be manufactured from any suitable laser or light conducting medium to obtain desired diffusion properties.

Groove 140 may be configured to fit around or about light-diffusing element 132 when the jaw members 110 and 120 are disposed in a closed position. Groove 140 may also have a reflective surface such that light emitted from light-diffusing element 132 may pass through tissue and subsequently be reflected back into tissue to form a desired illumination pattern. In some embodiments, groove 140 may have light absorbing properties and/or include a material having light absorbing properties (e.g., a light absorbent coating). In this manner, when light is absorbed, groove 140 and/or the absorbent material may heat to a suitable temperature to operably treat tissue held between jaw members 110 and 120.

During operation, once tissue is grasped between the tissue-contacting surfaces 112 and 122, laser light is transmitted from the energy source 40 to the light-diffusing element 132, which then emits light energy into the tissue. Since the tissue-contacting surfaces 112 and 122 are adapted to reflect light, the light energy emitted by the light-diffusing element 132 is concentrated in the volume between the jaw members 110 and 120 which, in turn, heats up the tissue grasped therebetween without compromising the surrounding tissue. After a preset duration or upon a signal from one or more sensors (described in further detail below), the energy is terminated indicating that the tissue treatment (e.g., seal or cutting) is complete.

Figure 3:
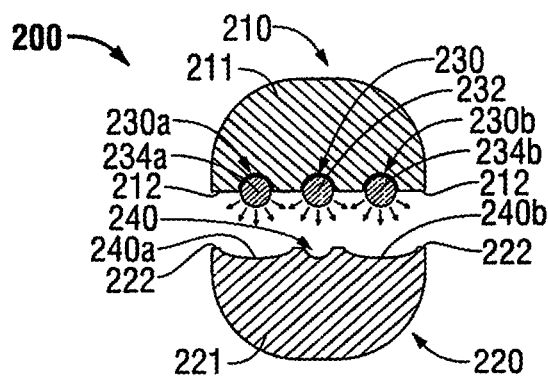
FIG. 3 is a front, cross-sectional view of an end effector assembly in accordance with another embodiment of the present disclosure.

Referring now to FIG. 3, another embodiment of the presently-disclosed end effector assembly is shown as end effector assembly 200. End effector assembly 200 includes jaw members 210 and 220 having tissue-contacting surfaces 212 and 222. Similar to the above discussed jaw members 110 and 120, jaw members 210 and 220 cooperate to grasp tissue therebetween. Each jaw member 210 and 220 defines channels or grooves disposed therealong. More specifically, jaw member 210 includes grooves 230, 230a, and 230b, and jaw member 220 includes grooves 240, 240a, and 240b. In some embodiments, jaw member 210 includes a plurality of laser light fibers (e.g., laser fiber 232, 234a, and 234b) that span along the length of the jaw member 210 and within respective grooves 230, 230a, and 230b. The laser fibers are configured to emit a laser light between and along the length of jaw members 210 and 220.

Jaw member 210 includes a centrally-positioned laser fiber 232 that is disposed within channel 230. Alongside of channel 230, jaw member 210 also defines channel or grooves 230a and 230b that are laterally positioned from channel 230 and include peripheral laser fibers 234a and 234b. The laser fibers 234a and 234b may be configured for sealing tissue, based on the type of light energy supplied thereto, pressure applied to the jaw members 210 and 220, as well the reflective or absorbing properties of the grooves disposed about the fibers as described in more detail below. In some embodiments, the tissue-contacting surfaces 212 and 222 may include a transparent coating or cover disposed on the surface thereof, similar to the tissue-contacting surfaces 112 and 122 of FIGS. 2A and 2B. The laser fiber 232 may be configured to cut tissue after an effective seal has been achieved by laser sealing fibers 234a and 234b. In some embodiments, cutting may be performed independent of the sealing. In addition, a reflective groove 240 may be disposed on the jaw member 220 such that when laser light is emitted from laser fiber 232, the laser light is reflected from reflective groove 240 back through tissue forming a desired illumination pattern. Additionally or alternatively, laser fibers 234a and 234b may also have respective reflective or absorbing grooves 240a and 240b within opposing jaw member 220, as described above.

It should be noted that any number of laser fibers may be used in any of the embodiments discussed in the present disclosure to achieve tissue sealing or cutting based on the light energy transmitted through the laser fibers. Similarly, any number of laser cutting fibers (e.g., laser fiber 232) may be used in any of the embodiments discussed in the present disclosure. In some embodiments, a single laser fiber may also be configured to include sealing and cutting capabilities in any of the embodiments of the present disclosure. It should be noted that any one of the laser fibers may be configured to transmit energy at different wavelengths depending on the surgical treatment (e.g., sealing, cutting and/or sensing). In other embodiments, a particular laser or light fiber may be configured to perform a particular surgical treatment (e.g., sealing, cutting and/or sensing). One or more sensors may be employed and/or a feedback circuit may be integrated with respect to end effector assembly 200 to signal the user after an effective seal and/or effective separation. An automated seal and cut algorithm may also be employed for this purpose that uses a single activation of a switch, e.g., switch 32, to initiate the process.

Figure 4A:
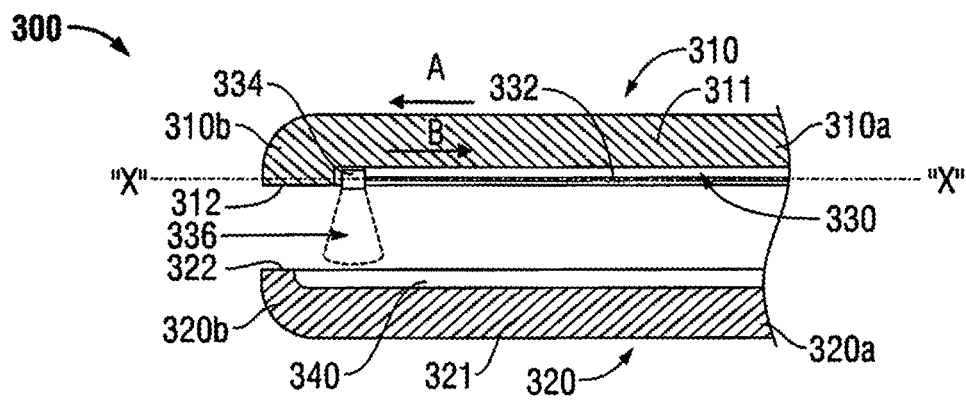
FIG. 4A is a side, cross-sectional view of an end effector assembly in accordance with another embodiment of the present disclosure.
Figure 4B:
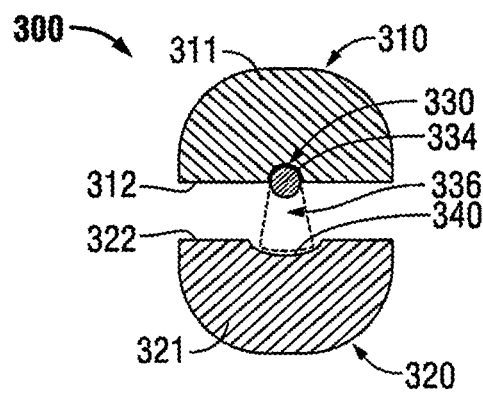
FIG. 4B is a front, cross-sectional view of the end effector assembly of FIG. 4A.
Figure 4C:
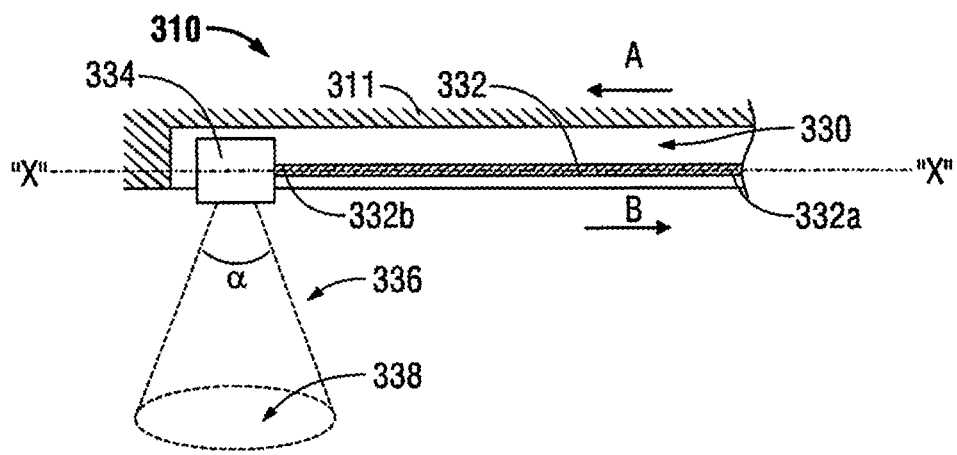
FIG. 4C is a side, schematic view of a laser fiber of the end effector assembly of FIG. 4A.

FIGS. 4A through 4C illustrate an embodiment of an end effector assembly 300 that includes jaw members 310 and 320 having proximal ends 310a, 320a, respectively, and distal ends 310b, 320b, respectively. Each jaw member 310 and 320 has a tissue-contacting surface 312 and 322, respectively. In some embodiments, the tissue-contacting surfaces 312 and 322 may include a transparent coating or cover disposed on the surface thereof, similar to the tissue-contacting surfaces 112 and 122 of FIGS. 2A and 2B. Additionally, jaw member 310 includes a channel or groove 330 defined therealong that is configured to include a surgical treatment laser fiber 332 (e.g., sealing, cutting and/or sensing) having proximal and distal ends 332a and 332b. Surgical treatment laser fiber 332 is configured to translate along a longitudinal axis "X-X", defined within jaw member 310, and within channel 330. For example, surgical treatment laser fiber 332 may be translated from proximal end 310a to distal end 310b of jaw member 310 (e.g., in a distal direction "A") to cut, seal and/or sense tissue being grasped between jaw members 310 and 320. Additionally or alternatively, surgical treatment laser fiber 332 may be translated from distal end 310b to proximal end 310a of jaw member 310 (e.g., in a proximal direction "B") to cut, seal and/or sense tissue being grasped therebetween. Surgical treatment laser fiber may be stationary within either one or both of the jaw members 310 and 320. In other embodiments, any other suitable type of light energy, including but not limited to laser light energy, may be transmitted by the aforementioned fibers (and/or other fiber pathways).

Referring to FIGS. 4A through 4C, the distal end of laser fiber 332b includes a laser emitter 334 that is configured to emit a laser beam into a defined solid angle 336 forming a desired illumination pattern. Laser fiber 332 may be a so-called "end-firing" or "side-firing" laser fiber. The term "end-firing" as used herein denotes a laser fiber that has the capability to emit a light along a longitudinal axis "X-X" defined by jaw member 310. The term "side-firing" as used herein denotes a laser fiber that has the capability to emit light (or any other suitable light energy) that is non-parallel to the longitudinal axis "X-X" of jaw member 310. Laser emitter 334 may include various components, such as one or more reflective surfaces (e.g., mirrors), one or more optical fibers, one or more lenses, or any other suitable components for emitting and/or dispersing a laser beam. More particularly, laser emitter 334 is configured to emit light into the solid angle 336 that has an outer boundary that may be variable or predetermined By varying or adjusting the solid angle 336, a laser target area 338 may be adjusted to vary the intensity of the laser light energy illuminating the tissue and the area of the tissue being treated, dissected or cut. Laser target area 338 may define any suitable target shape, for example, but not limited to an ellipse, rectangle, square and triangle. In some embodiments, laser emitter 334 may also be configured to seal and/or cut tissue grasped between the jaw members.

In addition to longitudinal movement of the laser emitter 334 along the longitudinal axis "X-X," the laser emitter 334 may also be rotated about the axis "X-X" and/or moved laterally (e.g., transverse) with respect thereto. Longitudinal, lateral, and rotational motion of the laser emitter 334 allows for directing light energy in any desired direction to accomplish desired tissue treatment effects.

Reflective groove(s) 340 may be made from a polished metal or a coating may be applied to the jaw member 320 if the jaw member 320 is formed from a non-metal and/or non-reflective material (e.g., plastic). The reflective groove 340 reflects laser light back through the tissue. Laser emitter 334 may receive the reflected laser light and transmit the signal back to energy source 40 for processing. Various types of data may be integrated and calculated to render various outcomes or control tissue treatment based on the transmitted or reflected light.

Figure 5:
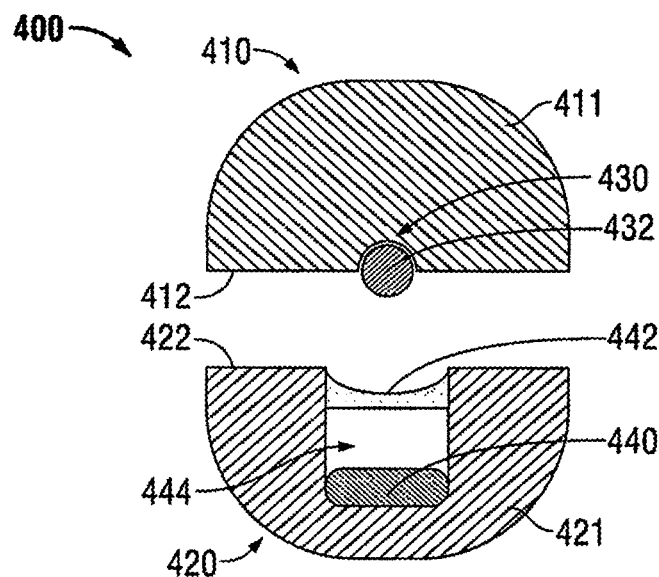
FIG. 5 is a front, cross-sectional view of an end effector assembly in accordance with another embodiment of the present disclosure.

FIG. 5 illustrates an embodiment of an end effector assembly 400 for forming a desired illumination pattern. End effector assembly 400 includes jaw members 410 and 420 having tissue-contacting surfaces 412 and 422. Similar to the above-described jaw members, jaw members 410 and 420 cooperate to grasp tissue therebetween. Jaw member 410 defines a channel or groove 430 therealong that is configured to include a laser fiber 432 that spans along jaw member 410 and is configured to emit a laser light within and along the length of jaw member 410. In some embodiments, the fiber 432 may be substituted by any laser source such as a fiber laser (e.g., tunable thalium fiber laser) described in this disclosure. In further embodiments, the tissue-contacting surfaces 412 and 422 may include a transparent coating or cover disposed on the surface thereof, similar to the tissue-contacting surfaces 112 and 122 of FIGS. 2A and 2B.

Jaw member 420 includes a receiving fiber 440 disposed within a cavity 444 defined therein that is configured to receive the laser light emitted from laser fiber 432. In some embodiments, the fiber 440 may be substituted by any optical detectors described in this disclosure or other suitable optical detectors. An optical window 442 is disposed along the surface of jaw member 420 between laser fiber 432 and receiving fiber 440. Optical window 442 may be any suitable type of optical lens configured to direct the laser light being emitted from laser fiber 432 to receiving fiber 440. Cavity 444 may be configured to contain a gas or any other medium to facilitate reception of laser light emitted by laser fiber 432 by receiving fiber 440.

Optical properties of tissue are known to change during heating. Properties such as the absorption coefficient ($\mu_a$), scattering coefficient ($\mu_s$), and anisotropy coefficient (g) have been shown to change as a function of temperature and time. These properties affect the transmission and reflection of light as it interacts with tissue. The present disclosure incorporates a receiving fiber 440 that may be used to detect and/or monitor changes in the transmission of laser light from laser fiber 432 through the tissue during a sealing cycle to determine when a desired tissue effect has been achieved. In this configuration, cut completion, e.g., when the tissue is separated, may also be detected and/or monitored using the receiving fiber 440.

Figure 6:
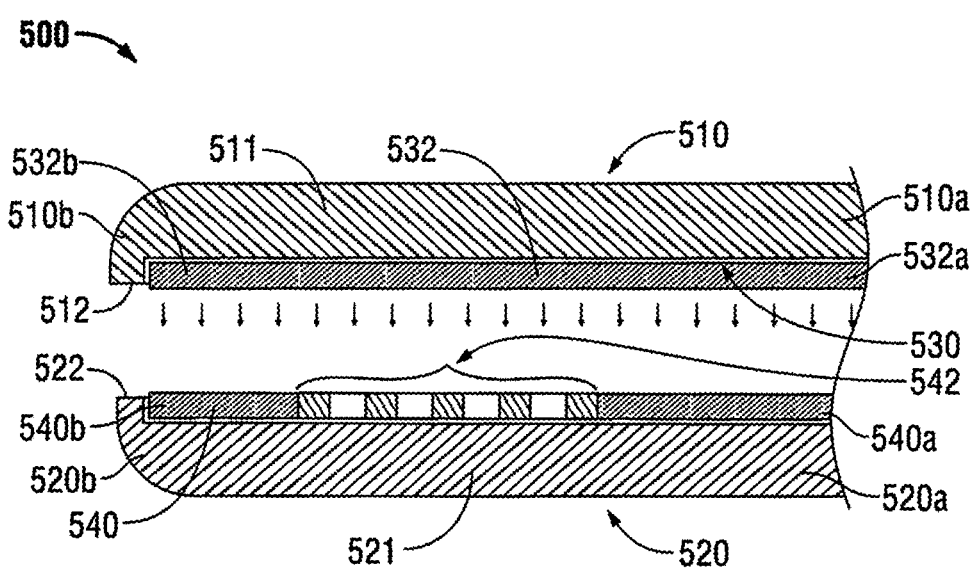
FIG. 6 is a side, cross-sectional view of an end effector assembly in accordance with another embodiment of the present disclosure.

FIG. 6 illustrates an embodiment of an end effector assembly (generally depicted as end effector assembly 500) for forming a desired illumination pattern. End effector assembly 500 includes jaw members 510 and 520 having tissue-contacting surfaces 512 and 522. Similar to the above-described jaw members, jaw members 510 and 520 cooperate to grasp tissue therebetween. Additionally, jaw member 510 defines a channel or groove 530 therealong that is configured to include a laser cutting fiber 532 that spans between proximal and distal ends 532a and 532b of jaw member 510. Laser fiber 532 is configured to emit a laser light within and along the length of jaw members 510 and 520. On an opposing side, a receiving fiber 540 is disposed within jaw members 520 and extends along a length thereof and is configured to receive the laser light emitted from laser fiber 532.

Receiving fiber 540 includes proximal and distal ends 540a and 540b and also includes one or more sensors 542 therebetween. Sensor(s) 542 is configured to monitor a temperature during a seal cycle and provide feedback as to when a seal cycle is complete. Since pressure is a factor in the quality of a seal following a sealing treatment, sensor 542 may also determine jaw pressure by measuring the strain in the jaw members 510 and 520 resulting from applied mechanical loads when tissue is grasped between jaw members 510, 520. In this configuration, feedback may be provided to an operator (and/or to the controller 42) as to whether the appropriate jaw pressure has been attained prior to energy activation to achieve a proper tissue seal.

Figure 7A:
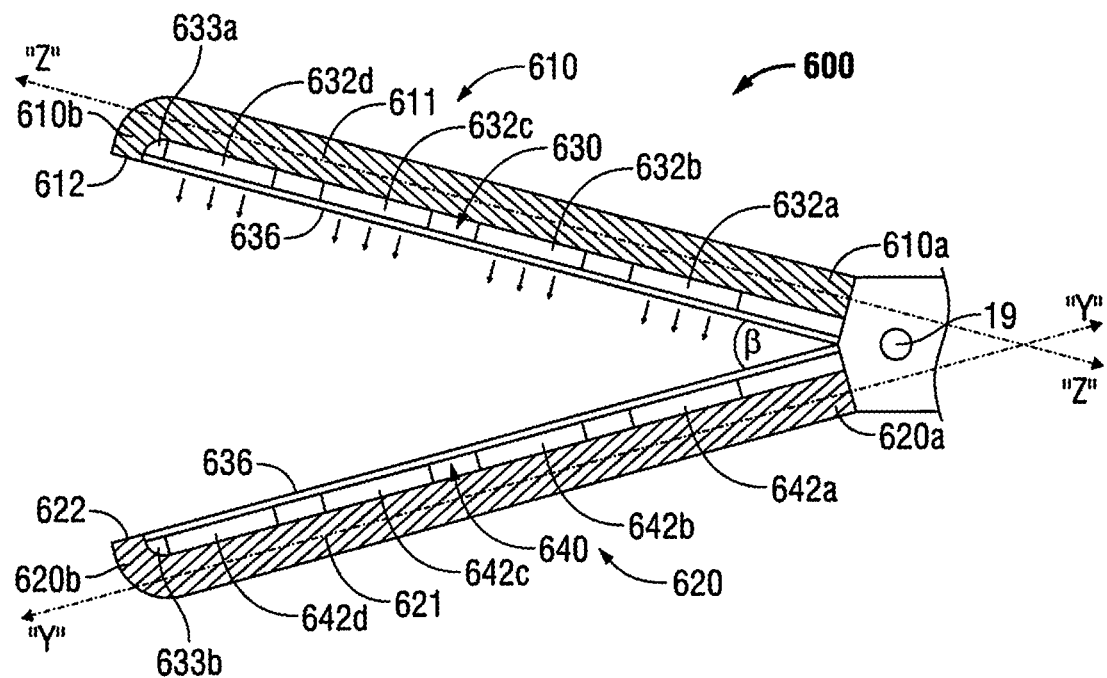
FIGS. 7A and 7B are side, cross-sectional views of an end effector assembly in accordance with another embodiment of the present disclosure.
Figure 7B:
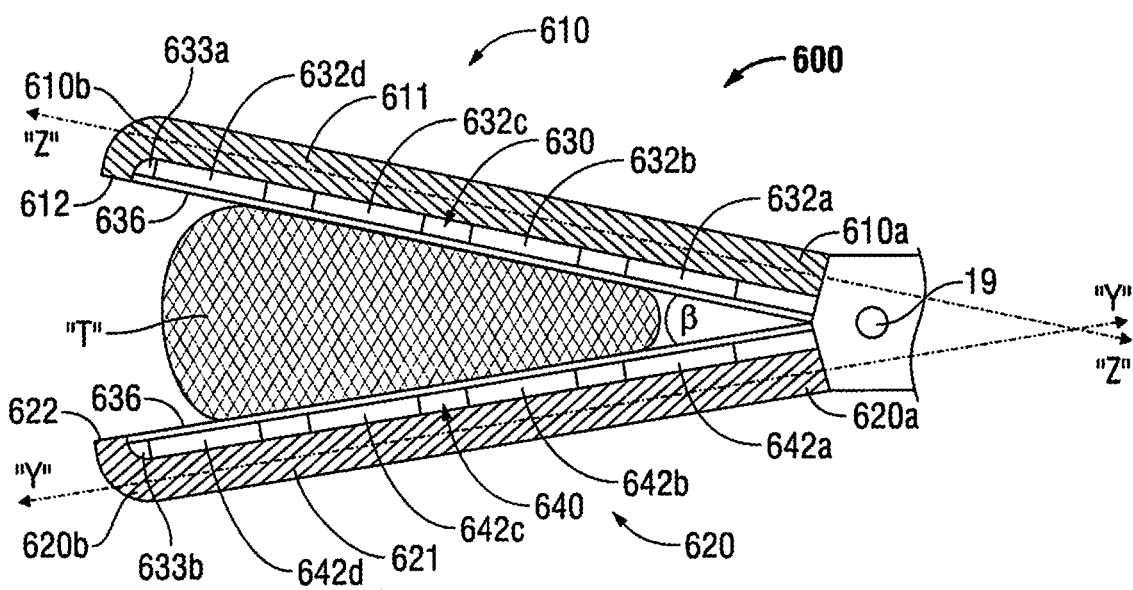

FIGS. 7A and 7B illustrate another embodiment of an end effector assembly 600 for forming a desired illumination pattern. End effector assembly 600 includes jaw members 610 and 620 having tissue-contacting surfaces 612 and 622. Similar to the above-described jaw members, jaw members 610 and 620 cooperate to grasp tissue therebetween. Jaw members 610 and 620 each define longitudinal axes "Z-Z" and "Y-Y," respectively, that span from their respective proximal ends 610a, 620b to their respective distal ends 610b, 620b. Longitudinal axes "Z-Z" and "Y-Y" define an angle "β" that increases as jaw members 610 and 620 are separated from each other, when pivoted from a closed configuration to an open configuration.

End effector assembly 600 includes one or more light-emitting elements 632a, 632b, 632c, and 632d that are disposed within a channel 630 defined along the length of jaw member 610. Each light-emitting element 632a, 632b, 632c, and 632d is configured to emit a light energy within and along the length of jaw members 610 and 620. Light-emitting elements 632a, 632b, 632c, and 632d may be any suitable type of light-emitting element, for example, but not limited to high-intensity LEDs configured for medical use and/or tissue treatment, optical fibers or other optical elements configured to emit light into the tissue. Light-emitting elements 632a, 632b, 632c, and 632d may be selectively activatable (e.g., one or a few at a time) and may emit light at different wavelengths. One or more light-receiving elements 642a, 642b, 642c, and 642d are disposed within a channel 640 defined along the length of jaw member 620. Each light-receiving element 642a, 642b, 642c, and 642d is configured to detect the light energy emitted from the light-emitting elements 632a, 632b, 632c, and 632d. The light-emitting elements 632a, 632b, 632c, and 632d and the light-receiving elements 642a, 642b, 642c, and 642d may be disposed behind a protective substrate 636 configured to transmit light.

The light-receiving elements 642a, 642b, 642c, and 642d may be any suitable light-receiving element, such as a lens, an optical fiber, or photodetector, and may be configured to measure optical properties of the tissue. In some embodiments, the light-receiving elements may collect and transmit light to optical systems configured to provide a variety of spectroscopic measurements including Raman spectroscopy, which is suitable for determining seal competition and identification of specific tissue types and its constituents (e.g., collagen, protein, water, etc.). Raman spectroscopy is described in more detail later in this description.

In some embodiments the light-receiving element 642a, 642b, 642c, and 642d and the light-emitting elements 632a, 632b, 632c, and 632d may be interspersed between the jaw members 610 and 620, such that each of the jaw members 610 and 620 includes one or more receiving modules and one or more light-emitting elements. This configuration provides for measuring optical properties (e.g., reflection and transmission data) at each jaw member 610 and 620 and allows for use of optical coherence tomography to obtain images of the tissue grasped between the jaw members 610 and 620. Other techniques for determining optical tissue properties are disclosed in a commonly-owned U.S. patent application Ser. No. 12/665,081 entitled "Method and System for Monitoring Tissue During an Electrosurgical Procedure," the entire contents of which is incorporated by reference herein.

Each light-emitting element 632a, 632b, 632c, and 632d may be configured to independently adjust its emittance of light energy along the jaw member 610 depending on angle "β." For example, when angle "β" is about 45 degrees (e.g., when jaw members 610 and 620 are moved towards an open configuration) the distal-most light-emitting element 632d may emit light energy with a greater intensity than the proximal-most light-emitting element 632a. As angle "β" decreases to about 2 degrees (e.g., when jaw members 610 and 620 are moved towards a closed configuration) light-emitting elements 632a, 632b, 632c, 632d are configured to emit light energy with substantially the same intensity.

Intensity of the light energy, including individual intensity as described above, transmitted through the light-emitting elements 632a, 632b, 632c, and 632d may be adjusted by the controller 42 based on the measured angle "β" and/or the gap distance between the jaw members 610 and 620. As used herein, the term "gap distance" as used herein denotes the distance between the tissue-contacting surfaces 612 and 622. Since the jaw members 610 and 620 are pivotable relative to each other, the angle "β" therebetween is directly related to the gap distance and the two concepts are used interchangeably. Angle "β" may be measured using any suitable proximity sensors 633a, 633b disposed within the jaw members 610 and 620, respectively. The sensors 633a, 633b may be coupled to the controller 42 and include, but are not limited to, Hall Effect sensors, RF based sensors, and the like. In some embodiments, the sensors 633a, 633b may be a pair of corresponding light transmitter/receiver elements. In particular, a sensor may be a light-emitting element (e.g., LED) paired with a photodetector (e.g., PIN diode).

In some embodiments, the angle "β" may be controlled to achieve a desired gap distance between the jaw members 610 and 620 to match the thickness of the tissue to the optical depth of the light energy. If the thickness of the tissue is not greater than the optical depth of the light being passed through the tissue, then the light energy is not going to be fully absorbed. This occurs if the tissue is compressed such that it is thinner than the optical depth of the light energy being used. In addition, if the tissue is not sufficiently compressed, light energy does not fully penetrate the compressed tissue resulting in non-uniform heating of the tissue. Controlling of the gap distance to substantially match the optical depth of the light energy with the thickness of the tissue ensures that light energy is optimally absorbed.

In some embodiments where the jaw members 610 and 620 include reflective surfaces, such as the jaw members 110 and 120, the angle "β" may also be controlled while taking into consideration the reflection of the light from the tissue-contacting surfaces 612 and 622.

The controller 42 obtains the angle "β" from the sensors 633a, 633b and determines the gap distance based on the measurement. The controller 42 also obtains the wavelength of the light energy being delivered by the energy source 40. This may be accomplished by storing a value of the wavelength in memory or any other computer-readable storage device which may be either transient (e.g., random access memory) or non-transient (e.g., flash memory). The controller 42 then calculates the desired gap distance based on the stored wavelength value and stored tissue properties. The controller 42 also compares the actual gap distance and/or angle "β" to desired gap distance and/or angle "β" as calculated based on the wavelength. Based on the comparison, the controller 42 may adjust the gap distance and/or angle "β" between the jaw members 610 and 620 automatically and/or output the difference for the user. Automatic adjustment may be accomplished by providing the jaw members 610 and 620 with automatic closure mechanisms such as those disclosed in commonly owned U.S. Pat. No. 7,491,202, entitled "Electrosurgical Forceps With Slow Closure Sealing Plates and Method of Sealing Tissue," which discloses automatic gap control for electrosurgical forceps, the entire contents of which is incorporated by reference herein.

For manual gap adjustment, the controller 42 may output the difference between actual and desired gap distance and/or angle "β" in an audio/visual manner. In some embodiments, the actual and desired gap distance and/or angle "β" or the difference therebetween may be represented numerically and/or graphically (e.g., color-coded). The difference may also be represented by audio alarms (e.g., adjusting frequency or amplitude of sound pulses).

As discussed in the previous embodiments, light-emitting elements 632a, 632b, 632c, and 632d and receiving modules 642a, 642b, 642c, and 642d may be configured to have optical sensing properties such that each pair of light-emitting element and receiving module (e.g., light-emitting element 632a and receiving module 642a) may be used to monitor the sealing process at a particular position. Light-emitting elements 632a, 632b, 632c, and 632d and receiving modules 642a, 642b, 642c, and 642d may also be configured to monitor the presence and state of other material in and around the sealing device and may also modify a sealing algorithm based upon the information collected.

In other embodiments, light-emitting elements 632a, 632b, 632c, and 632d and receiving modules 642a, 642b, 642c, and 642d may also be configured to inject a heat pulse and measure the response of tissue "T", measure spectral characteristics in transmission and/or reflection, measure spectral characteristics at different positions, measure spectral characteristics at different light frequencies. Light-emitting elements 632a, 632b, 632c, and 632d and receiving modules 642a, 642b, 642c, and 642d may also be configured to measure temperature at one or more locations between proximal and distal ends of jaw members 610 and 620.

Figure 8A:
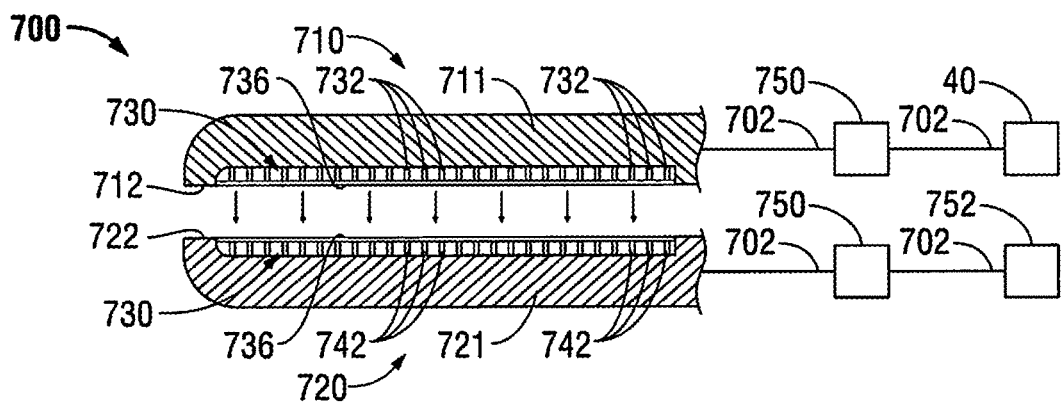
FIG. 8A is a side, cross-sectional view of an end effector assembly according to another embodiment of the present disclosure.
Figure 8B:
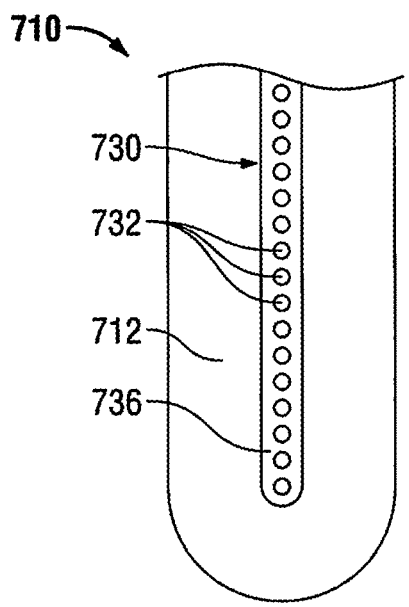
FIGS. 8B and 8C are top views of varying embodiments of end effector assemblies shown in FIG. 8A.
Figure 8C:
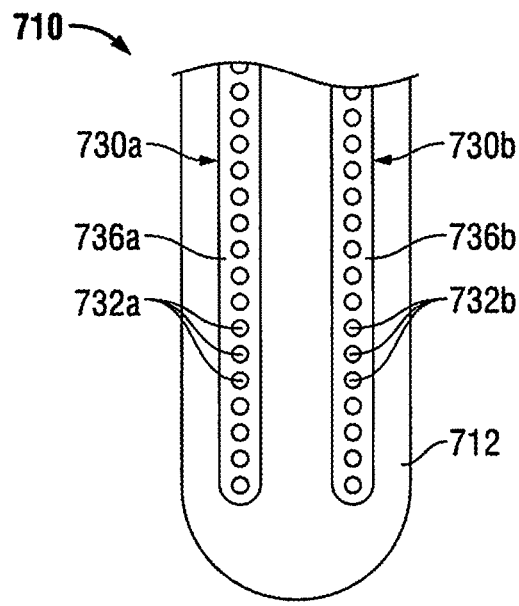

In FIGS. 8A through 8C, an embodiment of an end effector assembly 700 is shown for forming a desired illumination pattern. End effector assembly 700 includes jaw members 710 and 720 having tissue-contacting surfaces 712 and 722. Similar to the above-described jaw members, jaw members 710 and 720 cooperate to grasp tissue therebetween. Jaw members 710, 720 are operably connected to energy source 40 via an optical fiber 702 that provides light energy for treating tissue grasped between jaw members 710, 720. The optical fiber 702 may have any suitable shape, for example, but not limited to, rectangular, oval, and polygonal. In addition, distal end 1032a may also take the form of various suitable configurations (e.g., sharp or blunt).

Each jaw member 710, 720 includes one or more channels 730 having one or more vertically-aligned optical fibers 732 that are configured to emit and receive light energy from energy source 40 via optical fiber 702. In some embodiments, optical fibers 732 of jaw member 710 are vertically-aligned with optical fibers 742 of jaw member 720 such that optical communication is established. That is, one of the optical fibers is a transmitting optical fiber (e.g., optical fiber 732) and the opposing fiber is a receiving optical fiber (e.g., optical fiber 742). Any number of transmitting optical fibers 732 may be disposed about jaw member 710. Additionally or alternatively, any number of transmitting optical fibers 742 may be disposed about jaw member 720. Thus, in other embodiments, vertical alignment of optical fibers 732 and 742 is not particularly necessary.

In some embodiments, end effector assembly 700 may also include one or more optical switches 750 that provide selective activation and detection of light energy to and from jaw members 710 and 720 by an operator and/or energy source 40. Detection of light energy may be provided by an optical detector 752 or the like. In some embodiments, each channel 730 may be covered by a transparent cover 736 to allow optical communication between jaw members 710 and 720. It should be noted that any type of detecting device may be utilized with any of the embodiments presently disclose, for example, but not limited to photo diodes and charged coupled device (CCD) arrays.

FIG. 8B illustrates jaw member 710 having a single channel 730 defined therethrough that includes a plurality of optical fibers 732, as described above, that are covered by cover 736. Cover 736 may be any suitable material configured to allow optical communication between optical fibers 732 and 742. In another embodiment, FIG. 8C illustrates jaw member 710 defining a plurality of channels 730a and 730b therethrough and also includes a plurality of optical fibers 732 that are covered by cover 736.

As shown in FIGS. 9A and 9B, in further embodiments, a light dissection element 2445 may be disposed on an outer periphery of one of the jaw members 2110 and 2120. For sake of simplicity only a single jaw member, namely, the jaw member 2110 is discussed herein.

The dissection member 2445 may be a light-diffusing element, such as the light diffuser 132 described above with respect to FIGS. 2A and 2B. The dissection member 2445 is coupled via an optical fiber 2446 to the generator 40 and is disposed on or along at least a portion of an outer periphery 2110a of the jaw member 2110. As it is used herein, the term "outer periphery" denotes any surface of the jaw member 2110, such as the jaw housing 2116, that is not a tissue sealing contact surface 2112 or 2122. The dissection member 2445 may be selectively activated via the switch 2200 similar to the dissection member 2145 and may incorporate similar features, e.g., preventing light energy from being transmitted to the sealing surfaces 2112 and 2122 as described above with respect to the dissection member 2145.

Referring now to FIG. 10, an embodiment of an end effector assembly 1900 for forming a desired illumination pattern. End effector assembly 1900 includes jaw members 1910 and 1920 having tissue-contacting surfaces 1912 and 1922. Similar to the above-described jaw members, jaw members 1910 and 1920 cooperate to grasp tissue therebetween. Jaw members 1910, 1920 are operably connected via an optical fiber 1911 to a light energy source (e.g., generator 40). In particular, the optical fiber 1911 is coupled to the jaw member 1910. The light may be provided in different forms, including, but not limited to lasers, light-emitting diode, and any other suitable type of light energy.

The jaw member 1910 is formed from an optically transmissive material having an outer reflective coating 1910a. The transmissive material may be an optically diffusing material, such as, frosted sapphire crystal or an optically scattering material, such as polyoxymethylene, which is sold under a trademark DELRIN®, available from DuPont, Willmington, Del. The light from the optical fiber 1911 is transmitted to the jaw member 1910 and is contained therein by the reflective coating 1910a. This prevents the light from escaping outside the jaw member 1910 other than through the tissue-contacting surface 1912.

The jaw member 1920 may be formed from any optically absorbent or reflective tissue material. In some embodiments, the jaw member 1920 may include an optically absorbent or reflective coating 1920a on the tissue-contacting surface 1922. The coating 1920a and/or the jaw member 1920 block the light from passing through the jaw member 1920 concentrating the light energy at the tissue grasped between the jaw members 1910 and 1920.

Light energy is suitable for sealing tissue since it is converted into heat energy by absorption at a molecular level. In particular, certain molecules absorb light at certain wavelengths. In addition, as tissue is treated it undergoes physical and chemical changes, thus the wavelength at which light is optimally absorbed also changes. In some embodiments, light energy may be provided at two or more wavelengths to provide light energy that is optimally absorbed by two or more molecules (e.g., tissue types).

Figure 11:
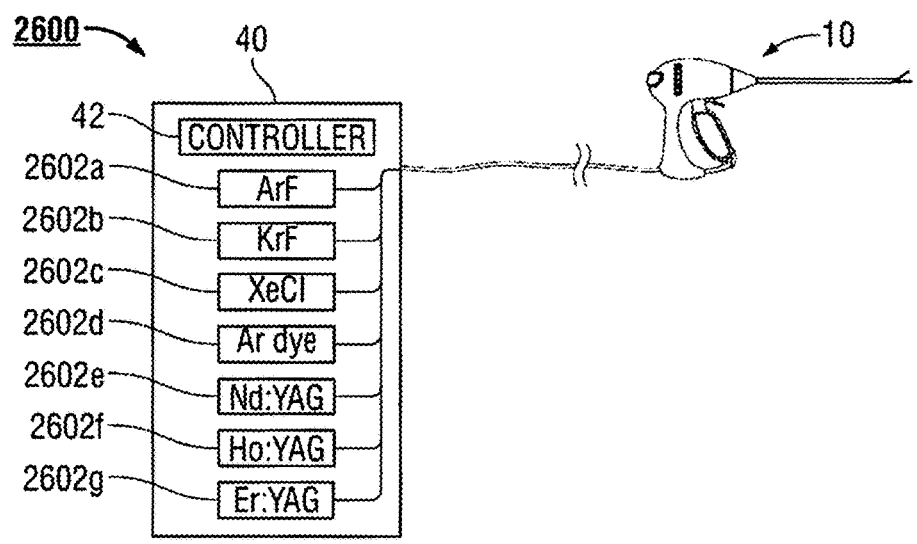
FIG. 11 is a schematic diagram of a surgical system in accordance with an embodiment of the present disclosure.

FIG. 11 shows a light energy surgical system 2600 including the energy source 40 and the forceps 10. The forceps 10 may include any of the embodiments of the jaw members described above. The generator 40 in combination with the forceps 10 may be utilized to generate light having a desired wavelength. The generator 40 may produce light energy at single or multiple wavelengths and may include a plurality of laser sources described above that are capable of producing light at multiple wavelengths. The generator 40 includes a plurality of laser light sources to generate laser light having a wavelength from about 100 nm to about 10,000 nm, which covers the majority of the tissue constituents. In particular, the generator 40 includes an ArF excimer laser 2602a, a KrF excimer laser 2602b, a XeCl excimer laser 2602c, an argon-dye laser 2602d, an Nd:YAG laser 2602e, an Ho:YAG laser 2602f, an Er:YAG laser 2602g.

Figure 12:
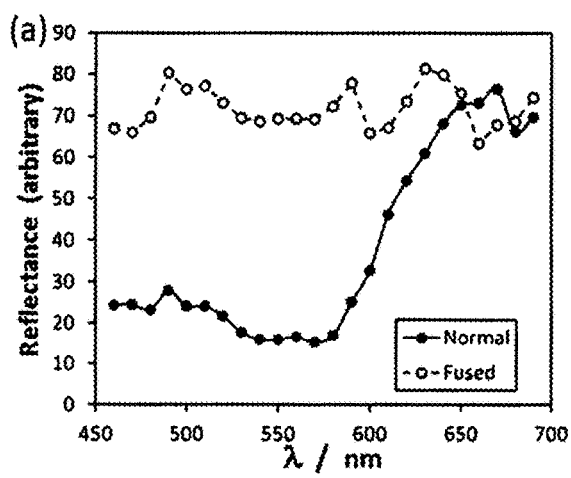
FIG. 12 is a plot of reflectance spectra from normal and fused tissue in accordance with an embodiment of the present disclosure.

The forceps 10 may be used to determine condition and composition of tissue, as described in further detail above with respect to FIGS. 7A and 7B. FIG. 12 shows a graph illustrating absorption of various tissue constituents as a function of the wavelength ranging from ultraviolet (UV) spectrum to infrared (IR) spectrum. Tissue constituents that are encountered in tissue include, but are not limited to water, vasculature, epidermis and other skin layers, whole blood, melanosome, collagen, and the like.

During operation, the forceps 10 is used to analyze tissue, including measuring the absorption thereof. The absorption measurements are analyzed by the controller 42 of the generator 40 which then determines which of the one or more laser light sources 2602a-2602g to activate to obtain optimal absorption of the light energy. The controller 42 may be coupled to a multiplexer (not shown) and/or another optical output switching apparatus to control activation of the laser light sources 2602a-2602g.

The forceps 10 may sense optical tissue properties continuously during the sealing procedure and to vary light energy output including intensity and which of the laser light sources 2602a-2602g are activated. Once it is determined that the sealing procedure is complete, the controller 42 may activate specific laser light sources 2602a-2602g most suitable for cutting sealed tissue.

Multispectral Method for Analyzing Tissue Samples

The embodiments described above may utilize a multispectral imaging (MSI) technique to acquire data before and after tissue fusions. A light-tissue interaction model comprising absorption and scattering terms is used to extract functional and structural information on normal and fused tissue from the measured spectral reflectance data. Before a tissue fusion procedure, the functional and structural information may be used to determine whether the tissue may undergo a successful fusion procedure. After a tissue fusion procedure, the functional and structural information may be used to determine whether the fusion procedure was successful.

The data acquired from the MSI technique may be used by a controller in an open ended or closed feedback loop to control the electrosurgical instrument.

The MSI technique may be used to measure reflected intensity from a standard surgical xenon light source across the 460-690 nm wavelength range. Motion artefacts due to breathing and peristalsis may be corrected by controller 42 using software. Wavelength-dependent changes in light source emission intensity and camera sensitivity may also be corrected controller 42 by normalising using a reference spectrum acquired from a white reflectance standard (Spectralon; Labsphere, Inc., USA). The attenuation spectrum, $A(\lambda)$, at a particular pixel location may then be calculated by taking the negative natural logarithm of this reflectance spectrum. The light loss is modelled by Eq. 1:

$$A(\lambda)[HbO_2]\varepsilon_{HbO_2}(\lambda)+[Hb]\varepsilon_{Hb}(\lambda)+a\lambda^{-b}+\alpha \qquad (1)$$

where $\lambda$ is wavelength, [HbO2] and [Hb] are the relative concentrations of oxy and deoxyhaemoglobin, $\varepsilon_{HbO2}(\lambda)$ and $\varepsilon_{Hb}(\lambda)$ are their known molar extinction coefficients, a and b are scattering-related parameters, and a is an offset term to account for spatial variations in illumination intensity. The relative haemoglobin concentrations are used to calculate total haemoglobin (Hbt=HbO$_2$+Hb) (a surrogate for blood volume) and oxygen saturation (SaO2=HbO$_2$/Hbt). The scattering term a$\lambda^{-b}$ is an empirical term combining Rayleigh and Mie contributions that describes the wavelength-dependent behavior of the reduced scattering coefficient, with b usually called the "scattering power". This scattering spectrum is scaled by the factor a.

The total haemoglobin and/or oxygen saturation pre-fusion values may be used by the controller 42 to determine if the tissue site is an optimum site to perform a tissue fusion procedure before commencement of the procedure. The range of total haemoglobin and/or oxygen saturation pre-fusion values may be, for example, from 20% to 80%, although other ranges are also contemplated. If the total haemoglobin and/or oxygen saturation values are not within the range, the controller 42 may power down the electrosurgical device and inform the clinician that the tissue site is unsuitable for a tissue fusion procedure and/or another tissue site should be chosen for performing a tissue fusion.

In other embodiments, after the tissue fusion procedure is performed, the total haemoglobin and/or oxygen saturation post-fusion values may be calculated using the MSI technique to determine if the tissue procedure was successful. If the post-fusion values are within a predetermined range of values, which, in some examples, may be less than pre-fusion values, the controller provides an indication to the clinician the tissue fusion was successful. If the post-fusion values are not in the appropriate range, the controller 42 notifies the clinician that the tissue fusion was unsuccessful.

Examples

In one example, the small intestine of a 45 kg white domestic pig was exposed in an open abdominal procedure (conducted under UK Home Office personal animal license (PIL) No. 70/24843 and project license (PPL) No. 8012639). A commercial tissue fusion device (Ligasure; Covidien PLC, USA) was then used to perform a full-width seal of the bowel. This experiment was part of a large series of over 30 procedures, during which the RF device was used to resect a bowel segment then form an anastomosis to restore continuity. Seven fusions made in the small bowel of a single subject were imaged with the MSI laparoscope.

A multispectral imaging laparoscope was used to measure reflected intensity from a standard surgical xenon light source (xenon 300; Karl Storz GmbH, Tuttlingen, Germany) across the 460-690 nm wavelength range. Motion artefacts due to breathing and peristalsis were corrected using custom-written software combining the speeded-up robust feature (SURF) detection algorithm and tracking. Wavelength-dependent changes in light source emission intensity and camera sensitivity were corrected by normalising by a reference spectrum acquired from a white reflectance standard (Spectralon; Labsphere, Inc., USA).

Figure 13:
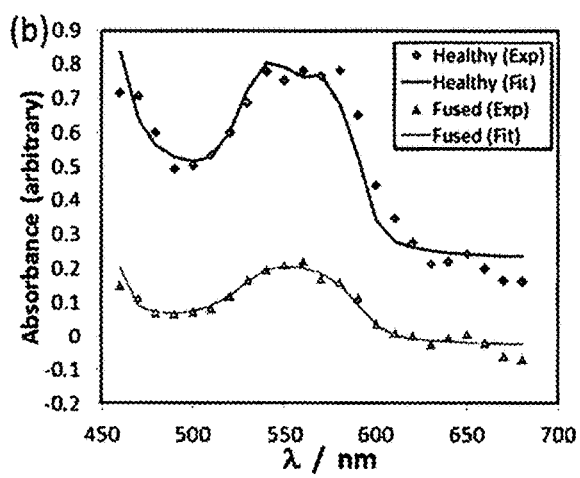
FIG. 13 is a plot of absorbance spectra from normal and fused tissue in accordance with an embodiment of the present disclosure.

FIG. 12 shows sample reflectance spectra from an area of normal and fused tissue. The normal tissue displays features associated with perfused tissue, such as low reflectance in the blue/green region (460-580 nm) and higher reflectance at red wavelengths. In contrast the sample spectrum from the fused area is comparatively flat. The calculated absorbance spectra shown in FIG. 13, taken from two separate sites, are plotted with their corresponding fits of Eq. 1. The distinctive spectral features of hemoglobin absorption are noticeable in both regions in the local minimum at 500 nm, peaks between 540 and 580 nm, and the marked decrease above 600 nm.

The main noticeable differences between the two curves are the decreased attenuation (increased reflectance) in the fused area and the markedly steeper slope in the 580-620 nm region in the healthy tissue. There is also a double-peak at 540 and 570 nm in the normal tissue, absent in the fused tissue, which is consistent with oxygenated hemoglobin.

The imaging results are shown in FIGS. 14A through 14D, which show a number of correlations with white light visual features. FIG. 14A is an RGB image reconstructed from the spectral datacube, FIG. 14B is an SaO2 overlay with transparency weighted by Hbt, FIG. 14C represents total haemoglobin showing low concentration in the fused region, and FIG. 14D represents scattering power b shows increased levels in the fused region. In cases where Eq. 1 represented a poor fit to the experimental spectra (coefficient of determination less than 0.9) the corresponding pixels in the processed image were excluded from calculations. This results in the unfilled and black regions shown in FIGS. 14B, 14C, and 14D. Compared to the healthy tissue the fused area has a significantly lower Hbt and SaO$_2$, but a higher scattering power.

The blank areas of the processed images in FIGS. 14A through 14D are due to both specular highlights, which result in saturation of the detector, and complete denaturation of the tissue. In the latter case the haemoglobin signal is absent and absorbance is relatively flat across the spectral range, as depicted in FIG. 12, leading to low fit quality.

The profiles of each of the model parameters, taken as an average in the vertical direction, across the images of FIGS. 14A through 14D are shown in FIGS. 15A through 15D. The border of the fused area is clearly discernible in each, with pronounced decreases in THb, SaO$_2$ and a. The scattering power in this case shows some structure but is elevated, particularly at the centre, in comparison to the normal tissue on either side.

Figure 15A:
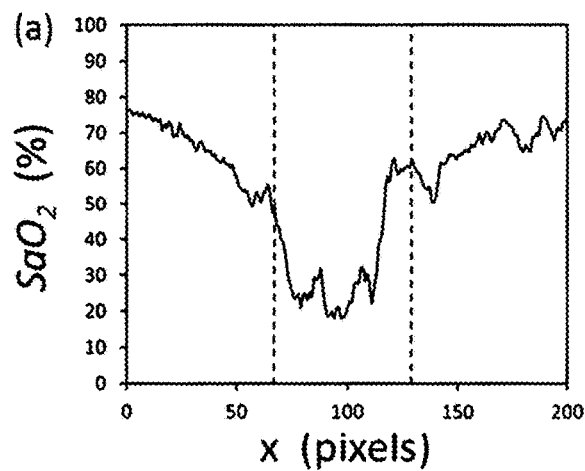
FIGS. 15A through 15D are profiles of fitting parameters showing the transition between normal and fused tissue in accordance with an embodiment of the present disclosure.
Figure 15B:
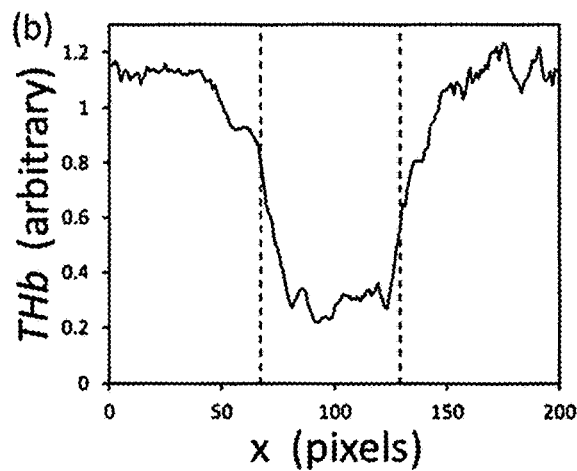
Figure 15C:
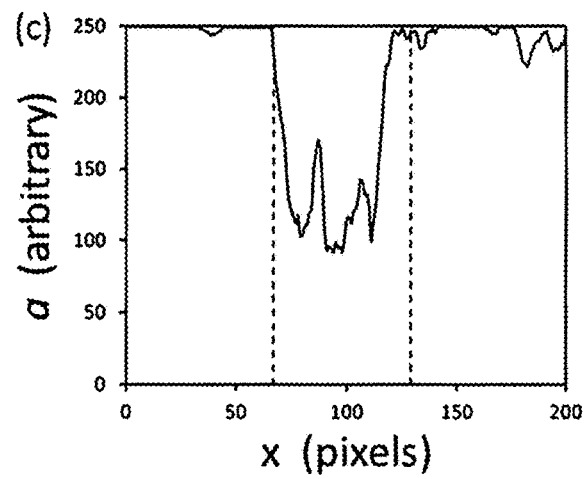
Figure 15D:
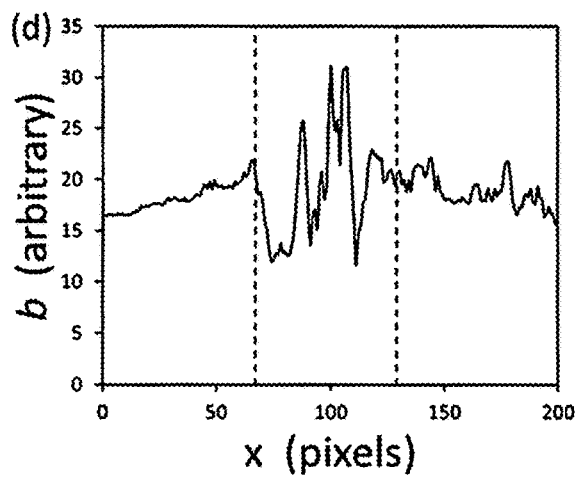

FIG. 15A represent oxygen saturation; FIG. 15B represents relative total haemoglobin concentration, FIG. 15C represents the scattering factor a, and FIG. 15D represents the scattering power b. The dashed lines indicate the visible borders of the fused region.

The average parameter values in 16 regions of interest (ROIs) across seven different fusions were calculated and the percentage difference between normal and fused areas determined. The resulting scatter plots are shown in FIGS. 16A through 16D (14A—SaO2; 14B—THb; 14C—scattering factor a; and 14D—scattering power b). Blood volume and oxygen saturation are consistently higher in normal tissue in comparison to fused, with average percentage differences of 70% and 22%, respectively. The scattering parameter a is marginally elevated in normal tissue, but by less than 1% on average. Scattering power b is strongly increased in fused tissue, with a mean difference of 131% across the regions examined.

A multispectral imaging laparoscope has been used to visualise intraoperative changes to the optical properties of porcine bowel tissue induced by a bipolar RF tissue fusion device. A model of light attenuation in tissue, incorporating an empirical scattering term, was used to extract functional and structural information. Higher reflectivity from the fused area can be explained by decreased absorption, due to low Hbt, and increased backscattering, most likely due to an increase in collagen cross-linking during heating. Although Hbt is significantly lower in the fused area, due to the combination of mechanical compression exerted by the jaws of the device and the application of RF energy, the features of the haemoglobin absorption spectrum are still visible in some cases. This may be due to blood trapped in capillaries during the heating process. Nevertheless in some parts of the tissue the denaturation is such that no recognisable haemoglobin features are visible and fitting of the model fails.

The profiles of the model parameters show clear distinction between fused and normal tissue, and combinations of these may be used to define the zone of tissue damage due to RF energy. Histological analysis of fused tissue in future studies will confirm the accuracy of this delineation. Simultaneous measurement of tissue autofluorescence due to collagen and elastin would also allow investigation of the correlation between scattering strength and the denaturation of the connective tissue.

In another example, fifteen bipolar RF induced side-to-side small bowel anastomoses (SSAs) were formed in vivo in three pigs using a commercial (LigaSure Impact™) and prototype RF sealing device, powered by a closed-loop, feedback controlled RF generator (Covidien, Boulder, Colo., USA). The prototype device was used to seal and divide a bowel segment and following adequate bowel alignment of the remaining proximal and distal bowel loops, two enterotomies were created. Each jaw of the LigaSure Impact™ device was placed into a single bowel lumen and clamped. RF energy was applied at a constant pressure and end impedance (100 ohms) but the speed of application (ramp) was varied resulting in a seal cycle between 10 and 100 s. On completion, the fused bowel was divided and the instrument advanced further into the two lumens. A total of four fusions were made to complete the neo-lumen formation. The enterotomy site was closed using the prototype sealer and oversewn with 3/0 vicryl. The anastomosis was returned to the abdominal cavity and re-examined prior to excision.

In total 15 anastomoses were formed (5 at each ramp level). The mean time to re-examination following completion was 153.9 minutes (38-311 minutes). Fourteen anastomoses (93%) were intact on assessment with one technical failure. All seals were found to be grossly viable with none of the intact anastomoses demonstrating leak when subjected to clinical stress. In addition, the seals in these anastomoses were fully formed on histological examination.

In yet another example, twenty-three small bowel anastomoses (15 RF-induced side-to-side using three energy algorithms (n=5), 4 hand-sewn end-to-end and 4 stapled side-to-side) were formed in six pigs and examined with a laparoscope-mounted xenon light source. Backscattered light from the tissue was collected and transmitted to an attached camera system. Sequential images were acquired of the tissue at multiple wavelengths of visible light (500-620 nm) to construct a reflectance spectrum at every point in the field-of-view. These were processed using a specifically developed algorithm to generate images showing relative concentrations of oxy- and deoxyhaemoglobin and hence, overall bowel oxygen saturation (SaO2). Six spectral measurements (three pre- and three post-anastomosis formation) were made at each anastomosis site to generate bowel SaO2 plots; from each of these, three 50×50 pixel regions of interest (ROIs) were selected for analysis. The mean pre- and post-anastomosis SaO2 were compared across all regions of interest using a two-sample t-test (N=414 ROIs).

Results

Anastomoses were imaged at a mean of 210 minutes after formation (range 38-420 minutes). Mean pre- and post-anastomosis SaO2 across the ROIs in the five anastomosis groups were as follows: bipolar RF energy algorithm 1 (56% vs. 36%; p=0.00004), bipolar RF energy algorithm 2 (55% vs. 41%; p=0.0054), bipolar RF energy algorithm 3 (66% vs. 35%; 0.00001), hand sewn (73% vs. 56%; p=0.0004), stapled (74% vs. 57%; p=0.0014). Anastomosis site multi spectral imaging demonstrated a statistically significant drop in tissue perfusion and oxygenation following the creation of all anastomoses.

A method of treating tissue in accordance with an embodiment of the present disclosure includes positioning an end effector assembly 100 (FIG. 1) including first and second jaw members 110 and 120 at a first position within tissue. The first and second jaw members 110 and 120 include tissue-contacting surfaces 112 and 122, respectively. At least one of the first and second jaw members 110 and 120 is movable from a spaced relation relative to the other jaw member to at least one subsequent position wherein the tissue-contacting surfaces 112 and 122 cooperate to grasp tissue therebetween. The method also includes activating a light-emitting element associated with one or both of the first and second jaw members 110 and 120 to emit light into tissue and evaluating one or more characteristics of the tissue based on a response to light entering the tissue.

Although embodiments have been described in detail with reference to the accompanying drawings for the purpose of illustration and description, it is to be understood that the disclosed processes and apparatus are not to be construed as limited thereby. It will be apparent to those of ordinary skill in the art that various modifications to the foregoing embodiments may be made without departing from the scope of the disclosure.

What is claimed is:

1. A forceps, comprising:
a housing;
a shaft coupled to the housing, the shaft having a proximal end and a distal end;
an end effector assembly disposed at the distal end of the shaft, the end effector assembly including first and second jaw members, at least one of the first or second jaw members movable from a first position wherein the first and second jaw members are disposed in spaced relation relative to one another to at least a second position closer to one another wherein the first and second jaw members cooperate to grasp tissue therebetween;
a plurality of light-emitting elements coupled to either one or both of the first and second jaw members, the plurality of light-emitting elements adapted to deliver light energy of different wavelengths to the tissue grasped between the first and second jaw members;
at least one light-detecting element configured to generate one or more signals indicative of tissue reflectance, wherein the plurality of light-emitting elements is configured to provide the different wavelengths for generating tissue reflectance indicative of a scattering spectrum in the tissue; and
a controller configured to collect data on the scattering spectrum based on the one or more signals and empirically determine a scattering power.

2. The forceps of claim 1, wherein at least one of the first and second jaw members including a groove defined therein having a reflective surface.

3. The forceps of claim 2, wherein the plurality of light-emitting elements is disposed within the groove.

4. The forceps of claim 1, further comprising an optical assembly coupled to the plurality of light-emitting elements, the optical assembly configured to convey the light energy emitted from the plurality of light-emitting elements to the tissue and to illuminate the tissue with a desired illumination pattern.

5. The forceps of claim 4, wherein the optical assembly includes at least one of an optical fiber, a refractive element, a reflective element, a diffracting element, and combinations thereof.

6. The forceps of claim 1, further comprising at least one tissue-contacting surface having a reflective element configured to reflect light passing through the tissue.

7. The forceps of claim 6, wherein the controller is further configured to determine whether a desired tissue effect has been achieved based on the one or more signals indicative of tissue reflectance.

8. The forceps of claim 1, further comprising a first electrically-conductive tissue-contacting surface associated with the first jaw member and a second electrically-conductive tissue-contacting surface associated with the second jaw member, wherein one of the first and second electrically-conductive tissue-contacting surfaces functions as an active electrode and the other one of the first and second electrically-conductive tissue-contacting surfaces functions as a return electrode during activation such that electrical energy flows from the active electrode through tissue positioned between the first and second electrically-conductive tissue-contacting surfaces to the return electrode.

9. The forceps of claim 7, wherein the desired tissue effect is tissue fusion and wherein the controller is configured to determine whether tissue fusion has been achieved based on the scattering power.

10. A forceps, comprising:
a housing;
a shaft coupled to the housing, the shaft having a proximal end and a distal end;
an end effector assembly disposed at the distal end of the shaft, the end effector assembly including first and second jaw members, at least one of the first or second jaw members movable from a first position wherein the first and second jaw members are disposed in spaced relation relative to one another to at least a second position closer to one another wherein the first and second jaw members cooperate to grasp tissue therebetween, at least one of the jaw members including at least one tissue-contacting surface having a reflective element configured to reflect light passing through the tissue;
a plurality of light-emitting elements coupled to either one or both of the first and second jaw members, the plurality of light-emitting elements adapted to deliver light energy of different wavelengths to the tissue grasped between the first and second jaw members;
at least one light-detecting element configured to generate one or more signals indicative of tissue reflectance, wherein the plurality of light-emitting elements is configured to provide the different wavelengths for generating tissue reflectance indicative of a scattering spectrum in the tissue; and
a controller configured to collect data on the scattering spectrum based on the one or more signals and empirically determine a scattering power, wherein the controller is further configured to determine whether a desired tissue effect has been achieved based on the one or more signals indicative of tissue reflectance,
wherein the desired tissue effect is tissue fusion and wherein the controller is configured to determine whether tissue fusion has been achieved based on the scattering power.

* * * * *